United States Patent
Kaminsky et al.

(10) Patent No.: US 10,280,464 B2
(45) Date of Patent: May 7, 2019

(54) DNA METHYLATION AND GENOTYPE SPECIFIC BIOMARKER OF SUICIDE ATTEMPT AND/OR SUICIDE IDEATION

(71) Applicant: THE JOHNS HOPKINS UNIVERSITY, Baltimore, MD (US)

(72) Inventors: Zachary Kaminsky, Baltimore, MD (US); Holly Wilcox, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 71 days.

(21) Appl. No.: 14/904,233

(22) PCT Filed: Jul. 11, 2014

(86) PCT No.: PCT/US2014/046280
§ 371 (c)(1),
(2) Date: Jan. 11, 2016

(87) PCT Pub. No.: WO2015/006645
PCT Pub. Date: Jan. 15, 2015

(65) Prior Publication Data
US 2016/0153044 A1    Jun. 2, 2016

Related U.S. Application Data

(60) Provisional application No. 61/844,996, filed on Jul. 11, 2013, provisional application No. 61/890,402, filed on Oct. 14, 2013.

(51) Int. Cl.
*C07H 21/04* (2006.01)
*C12Q 1/68* (2018.01)
*C12Q 1/6883* (2018.01)

(52) U.S. Cl.
CPC ..... *C12Q 1/6883* (2013.01); *C12Q 2600/154* (2013.01)

(58) Field of Classification Search
None
See application file for complete search history.

(56) References Cited

U.S. PATENT DOCUMENTS

2007/0065821 A1    3/2007    Kudaravalli et al.

FOREIGN PATENT DOCUMENTS

| WO | 1993-22458 A1 | 11/1993 |
| WO | 2008144371 A1 | 11/2008 |
| WO | 2010-066000 A1 | 6/2010 |

OTHER PUBLICATIONS

Perlegen (dbSNP ss24087298, Aug. 2004).*
Mehta et al. (PNAS, vol. 110, No. 20, pp. 8302-8307, May 14, 2013).*
Falcone, T., et al., "Serum S100B: a potential biomarker for suicidality in adolescents?" PLoS ONE (Jun. 2010) vol. 5, No. 6, e11089.
Murphy, T., et al., "Risk and protective genetic variants in suicidal behaviour: association with SLC1A2, SLC1A3, 5-HTR1B & NTRK2 polymorphisms" Behavioural and Brain Funnctions (2011) vol. 7, No. 22.
Zhang L. et al. "P11 (S100A10) as a potential biomarker of psychiatric patients at risk of suicide" Journal of Psychiatric Research (2011) vol. 45, pp. 435-441.
Posner et al (2011) The Columbia-Suicide Severity Rating Scale: initial validity and internal consistency findings from three multisite studies with adolescents and adults. Am J Psychiatry. Dec. 2011;168(12):1266-77. doi: 10.1176/appi.ajp.2011.10111704.
Kamali et al (2012) Associations between suicide attempts and elevated bedtime salivary cortisol levels in bipolar disorder. J Affect Disord. Feb. 2012;136(3):350-8. doi: 10.1016/j.jad.2011.11.027. Epub Dec. 10, 2011.
Lindqvist et al (2008) Salivary cortisol and suicidal behavior—a follow-up study. Psychoneuroendocrinology. Sep. 2008;33(8):1061-8. doi: 10.1016/j.psyneuen.2008.05.012. Epub Jul. 30, 2008.
Murphy et al (2013) Genetic variation in DNMT3B and increased global DNA methylation is associated with suicide attempts in psychiatric patients. Genes Brain Behav. Feb. 2013;12(1):125-32. doi: 10.1111/j.1601-183X.2012.00865.x. Epub Oct. 26, 2012.
Lindqvist et al (2011) CSF biomarkers in suicide attempters—a principal component analysis. Acta Psychiatr Scand. Jul. 2011;124(1):52-61. doi: 10.1111/j.1600-0447.2010.01655.x. Epub Dec. 28, 2010.
Zhang et al (2011) P11 (S100A10) as a potential biomarker of psychiatric patients at risk of suicide. J Psychiatr Res. Apr. 2011;45(4):435-41. doi: 10.1016/j.jpsychires.2010.08.012. Epub Sep. 22, 2010.
Laje et al (2009) Genome-wide association study of suicidal ideation emerging during citalopram treatment of depressed outpatients. Pharmacogenet Genomics. Sep. 2009;19(9):666-74. doi: 10.1097/FPC.0b013e32832e4bcd.
Laje et al (2007) Genetic markers of suicidal ideation emerging during citalopram treatment of major depression. Am J Psychiatry. Oct. 2007;164(10):1530-8.
Guintivano et al (2013) A cell epigenotype specific model for the correction of brain cellular heterogeneity bias and its application to age, brain region and major depression. Epigenetics. Mar. 2013;8(3):290-302. doi: 10.4161/epi.23924. Epub Feb. 20, 2013.

(Continued)

*Primary Examiner* — Jeanine A Goldberg
(74) *Attorney, Agent, or Firm* — Johns Hopkins Technology Ventures

(57) ABSTRACT

The present invention relates to the field of biomarkers. More specifically, the present invention relates to the use of biomarkers to predict suicide ideation and/or suicide attempt. In one embodiment, a method for predicting suicide ideation and/or attempt by a subject comprises the steps of (a) measuring the DNA methylation level of a CpG dinucleotide in the 3' untranslated region of SKA2; (b) identifying the genotype at a SNP within the 3' UTR of SKA2, and (c) predicting suicide ideation and/or attempt by the subject using a prediction algorithm.

13 Claims, 7 Drawing Sheets
Specification includes a Sequence Listing.

(56) References Cited

OTHER PUBLICATIONS

Birmaher et al (1999) Psychometric properties of the Screen for Child Anxiety Related Emotional Disorders (SCARED): a replication study. J Am Acad Child Adolesc Psychiatry. Oct. 1999;38(10):1230-6.

Cox et al (1987) Detection of postnatal depression. Development of the 10-item Edinburgh Postnatal Depression Scale. Br J Psychiatry. Jun. 1987;150:782-6.

Cohen et al (1983) A global measure of perceived stress. J Health Soc Behav. Dec. 1983;24(4):385-96.

Kellam et al (1991) Developmental epidemiologically based preventive trials: baseline modeling of early target behaviors and depressive symptoms. Am J Community Psychol. Aug. 1991;19(4):563-84.

Kellam et al (1994) The course and malleability of aggressive behavior from early first grade into middle school: results of a developmental epidemiologically-based preventive trial. J Child Psychol Psychiatry. Feb. 1994;35(2):259-81.

Rice et al (2008) Identification and functional analysis of SKA2 interaction with the glucocorticoid receptor. J Endocrinol. Sep. 2008;198(3):499-509. doi: 10.1677/JOE-08-0019. Epub Jun. 26, 2008.

Cao et al (2010) Intronic miR-301 feedback regulates its host gene, ska2, in A549 cells by targeting MEOX2 to affect ERK/CREB pathways. Biochem Biophys Res Commun. Jun. 11, 2010;396(4):978-82. doi: 10.1016/j.bbrc.2010.05.037. Epub May 12, 2010.

Karmaka et al (2013) Interaction of glucocorticoid receptor (GR) with estrogen receptor (ER) α and activator protein 1 (AP1) in dexamethasone-mediated interference of ERα activity. J Biol Chem. Aug. 16, 2013;288(33):24020-34. doi: 10.1074/jbc.M113.473819. Epub Jun. 28, 2013.

Langelder et al (2008) WGCNA: an R package for weighted correlation network analysis. BMC Bioinformatics. Dec. 29, 2008;9:559. doi: 10.1186/1471-2105-9-559.

Guintivano et al (2013) Antenatal prediction of postpartum depression with blood DNA methylation biomarkers. Mol Psychiatry. May 2014;19(5):560-7. doi: 10.1038/mp.2013.62. Epub May 21, 2013.

Le-Niculescu et al (2013) Discovery and validation of blood biomarkers for suicidality. Mol Psychiatry. Dec. 2013;18(12):1249-64. doi: 10.1038/mp.2013.95. Epub Aug. 20, 2013.

Rayssiguier et al (2010) Magnesium deficiency and metabolic syndrome: stress and inflammation may reflect calcium activation. Magnes Res. Jun. 2010;23(2):73-80. doi: 101684/mrh.2010.0208. Epub May 31, 2010.

Bali et al (2013) Implicating the role of plasma membrane localized calcium channels and exchangers in stress-induced deleterious effects. Eur J Pharmacol. Aug. 15, 2013;714(1-3):229-38. doi: 10.1016/j.ejphar.2013.06.010. Epub Jun. 21, 2013.

Reznikov et al (2008) [Calcium-dependent mechanisms of stress disorders and noradrenergic responses of the hypothalamo-pituitary-adrenal system in neonatally androgenized female rats]. Fiziol Zh. 2008;54(6):24-9.

Nock et al (2009) Cross-national analysis of the associations among mental disorders and suicidal behavior: findings from the WHO World Mental Health Surveys. PLoS Med. Aug. 2009;6(8):e1000123. doi: 10.1371/journal.pmed.1000123. Epub Aug. 11, 2009.

Bougea et al (2013) Effect of the emotional freedom technique on perceived stress, quality of life, and cortisol salivary levels in tension-type headache sufferers: a randomized controlled trial. Explore (NY). Mar.-Apr. 2013;9(2):91-9. doi: 10.1016/j.explore.2012.12.005.

Shonkoff et al (2012) The lifelong effects of early childhood adversity and toxic stress. Pediatrics. Jan. 2012;129(1): e232-46. doi: 10.1542/peds.2011-2663. Epub Dec. 26, 2011.

Turecki et al (2012) The neurodevelopmental origins of suicidal behavior. Trends Neurosci. Jan. 2012;35(1):14-23. doi: 10.1016/j.tins.2011.11.008. Epub Dec. 15, 2011.

Balleine et al (2010) Human and rodent homologies in action control: corticostriatal determinants of goal-directed and habitual action. Neuropsychopharmacology. Jan. 2010;35(1):48-69. doi: 10.1038/npp.2009.131.

Van Den Bos et al (2009) The role of the ventral medial prefrontal cortex in social decision making. J Neurosci. Jun. 17, 2009;29(24):7631-2. doi: 10.1523/JNEUROSCI.1821-09.2009.

Coryell et al (2001) The dexamethasone suppression test and suicide prediction. Am J Psychiatry. May 2001;158(5):748-53.

Ridder et al (2005) Mice with genetically altered glucocorticoid receptor expression show altered sensitivity for stress-induced depressive reactions. J Neurosci. Jun. 29, 2005;25(26):6243-50.

Smalheiser et al (2012) MicroRNA expression is down-regulated and reorganized in prefrontal cortex of depressed suicide subjects. PLoS One. 2012;7(3):e33201. doi: 10.1371/journal.pone.0033201. Epub Mar. 9, 2012.

Morlando et al (2008) Primary microRNA transcripts are processed co-transcriptionally. Nat Struct Mol Biol. Sep. 2008;15(9):902-9.

Choi et al (2010) Contrasting chromatin organization of CpG islands and exons in the human genome. Genome Biol. 2010;11(7):R70. doi: 10.1186/gb-2010-11-7-r70. Epub Jul. 5, 2010.

Bani-Fatemi et al (2013) Analysis of CpG SNPs in 34 genes: association test with suicide attempt in schizophrenia. Schizophr Res. Jul. 2013;147(2-3):262-8. doi: 10.1016/tschres.2013.04.018. Epub May 14, 2013.

Keller et al (2011) TrkB gene expression and DNA methylation state in Wernicke area does not associate with suicidal behavior. J Affect Disord. Dec. 2011;135(1-3):400-4. doi: 10.1016/j.jad.2011.07.003. Epub Jul. 29, 2011.

Labonte et al (2013) Genome-wide methylation changes in the brains of suicide completers. Am J Psychiatry. May 2013;170(5):511-20. doi: 10.1176/appi.ajp.2012.12050627.

Labonte et al (2012) Differential glucocorticoid receptor exon 1(B), 1(C), and 1(H) expression and methylation in suicide completers with a history of childhood abuse. Biol Psychiatry. Jul. 1, 2012;72(1):41-8. doi: 10.1016/j.biopsych.2012.01.034. Epub Mar. 22, 2012.

Fiori et al (2011) Genes Brain Behav. Feb. 2013;12(1):125-32. doi: 10.1111/j.1601-183X.2012.00865.x. Epub Oct. 26, 2012. J Psychiatr Res. Sep. 2011;45(9):1229-35. doi: 10.1016/j.jpsychires.2011.03.015. Epub Apr. 17, 2011.

* cited by examiner

DNA METHYLATION AND GENOTYPE SPECIFIC BIOMARKER OF SUICIDE ATTEMPT AND/OR SUICIDE IDEATION

CROSS-REFERENCE TO RELATED APPLICATIONS

This application is a 35 U.S.C. § 371 U.S. national entry of International Application PCT/US2014/046280, having an international filing date of Jul. 11, 2014, which claims the benefit of U.S. Provisional Application No. 61/844,996, filed Jul. 11, 2013, and U.S. Provisional Application No. 61/890,402, filed Oct. 14, 2013, the content of each of the aforementioned applications is herein incorporated by reference in their entirety.

STATEMENT OF GOVERNMENTAL INTEREST

This invention was made with government support under grant no. 1R21MH094771-01, awarded by the National Institutes of Health. The government has certain rights in the invention.

FIELD OF THE INVENTION

The present invention relates to the field of biomarkers. More specifically, the present invention relates to the use of biomarkers to predict suicide attempt and/or ideation.

INCORPORATION-BY-REFERENCE OF MATERIAL SUBMITTED ELECTRONICALLY

This application contains a sequence listing. It has been submitted electronically via EFS-Web as an ASCII text file entitled "P12394-03_ST25.txt." The sequence listing is 2,326 bytes in size, and was created on Jul. 11, 2014. It is hereby incorporated by reference in its entirety.

BACKGROUND OF THE INVENTION

Early life trauma is thought to influence numerous biological systems that affect the ability of an individual to properly manage stress later in life. Early life trauma can result in reduced cognitive abilities, increased impulsivity and increased risk for psychiatric disorders including post-traumatic stress disorder (PTSD), alcohol and drug use disorders and mood disorder, all of which could contribute to aberrant stress response and increased risk for fatal and nonfatal suicidal behaviors[5]. A growing body of evidence implicates epigenetic alterations in molecular pathways important for hypothalamic pituitary adrenal (HPA) axis function and sensitivity. For example, DNA methylation changes in the NR3C1 gene that encodes the glucocorticoid receptor (GR) are altered by maternal behavior in rats[12] and are elevated in the hippocampus of suicide completers that experienced early life trauma[13]. The cumulative effect of these epigenetically mediated events is a reduction in GR levels that may lead to an improper ability to manage stress in later life. While a majority of research has focused on NR3C1, identification of molecular variation at other genes within this pathway may represent important mediators of stress and suicidal behavior.

Suicide represents a major public health problem with the rates of death by suicide surpassing that of motor vehicle accidents in 2009[1]. More people die by suicide every year than homicides and all wars combined worldwide[2]. Suicide and suicide attempt are complex and heterogeneous phenotypes that have been a fairly intractable public health problem as annual suicide rates have been stable over the past 60 years at around 10 to 12 per 100,000[3], irrespective of advances in the diagnosis and treatment of major mental disorders. Psychiatric illness is present in 90% of suicides and suicide attempters[4] yet psychiatric illness is not sufficient to cause suicide phenotypes. Numerous factors have been demonstrated to influence suicide rates including but not limited to major depression, drug and alcohol abuse, stress, and traumatic events experienced during childhood such as assault and sexual abuse[2,5-11]. A growing consensus in the field is that suicidal behavior appears to resemble a stress response.

In light of converging evidence implicating alteration of the stress pathway with suicidal behavior, an attractive candidate for preemptively predicting suicide risk are stress hormone levels, which act as agonists for the GR. Glucocorticoids represent one of the most consistent factors associated with suicide based on both epidemiological[14-16] and molecular[17-19] evidence. Additionally, measuring an individual's cortisol response to stress has been identified as a promising endophenotype associated with suicide[20]; however, glucocorticoid levels vary drastically over the course of the day and as such cannot be easily used as a biomarker of suicide risk. Additionally, there are a number of conflicting reports on either elevated or reduced glucocorticoid responsiveness in response to early life stressors.[21] Importantly, the response of an individual to environmental factors such as stress may vary based on underlying biological susceptibility, mediated potentially by genetic factors. This gene X environment interaction hypothesis has been called the diathesis-stress or dual risk hypothesis, whereby an underlying biological state mediates a highly negative reaction to stress.[22-26] In light of this model, identification of the underlying genetic or epigenetic factors mediating risk to stressors would be required in order to develop an effective biomarker for stress and trauma associated morbidities such as suicidal behavior.

SUMMARY OF THE INVENTION

The present invention is based, at least in part, on the discovery of a biomarker capable of predicting suicide attempt and/or suicide ideation based on both genotype and DNA methylation status of a single CpG. Suicide is a major public health problem where environmental insults are thought to interact with underlying biological risk to mediate suicidal behavior. Suicidal thoughts, also known as suicidal ideation, are thoughts about how to kill oneself, which can range from a detailed plan to a fleeting consideration. Using a genome-wide DNA methylation scan, a combined epigenetic and genetic association with suicide was identified at rs7208505 within the 3'UTR of the SKA2 gene in post mortem cortical samples. Locus specific evaluation demonstrated a consistent association across the NICHD and SMRI brain cohorts. A replication was observed in peripheral blood with suicide attempt in the GenRED offspring cohort and with suicidal ideation in a prospective cohort. Genetic and epigenetic variation significantly interacted with salivary cortisol or perceived stress to account for between 75 and 96% of the suicidal behavior variation. Epigenetic variation was significantly associated with suicide attempts in a population based cohort of 326 individuals when accounting for alcohol abuse. Statistical modeling predicted suicidal behavior across all peripheral blood cohorts with an accuracy ranging from 72~96%. Our findings implicate SKA2 as a novel genetic and epigenetic target involved in suicide diathesis.

Accordingly, in one aspect, the present invention provides methods for predicting suicide ideation and/or suicide attempt. In particular embodiments, the methods of the present invention can be administered to children at perceived risk or to military service men and women, for example, during basic training. In one embodiment, a method for predicting suicide attempt and/or suicide ideation by a subject comprising the steps of (a) measuring the DNA methylation level of a CpG located on the minus strand of chromosome 17, at position 57187729, from DNA isolated from a sample collected from the subject; (b) identifying the genotype at the single nucleotide polymorphism (SNP), rs7208505, from DNA isolated from a sample collected from the subject; and (c) predicting suicide attempt and/or suicide ideation by the subject using a linear model that utilizes the DNA methylation level, genotype at rs7208505, age and sex. In a further embodiment, the linear model further utilizes a stress/anxiety metric.

In another specific embodiment, a method for predicting suicide attempt and/or suicide ideation by a subject comprising the steps of (a) measuring the DNA methylation level of a CpG located on the minus strand of chromosome 17, at position 57187729, from DNA isolated from a sample collected from the subject; (b) identifying the genotype at the single nucleotide polymorphism (SNP), rs7208505, from DNA isolated from a sample collected from the subject; and (c) predicting suicide attempt and/or suicide ideation by the subject using a linear model thatutilizes the DNA methylation level, genotype at rs7208505, age, sex and a stress/anxiety metric.

The present invention also provides a method for predicting suicide ideation and/or suicide attempt comprising the steps of (a) measuring DNA methylation level at a CpG dinucleotide located in the 3' untranslated region (UTR) of SKA2 from DNA isolated from a sample collected from the subject; (b) identifying the genotype at the SNP rs7208505, from DNA isolated from a sample collected from the subject; and (c) predicting suicide attempt and/or suicide ideation by the subject using a linear model that incorporates the measured DNA methylation level and genotype. In a specific embodiment, the CpG dinucleotide in the 3' UTR of SKA2 is located on the minus strand of chromosome 17, at position 57187729. In certain embodiments, the linear model further utilizes age and sex as additive covariates. In yet another embodiment, the linear model further utilizes a stress/anxiety metric.

In a specific embodiment, the stress/anxiety metric comprises the results from a stress/anxiety questionnaire. In an alternative embodiment, the stress/anxiety metric comprises salivary cortisol measurement from the subject. In another embodiment, the stress/anxiety metric comprises a biomarker of salivary cortisol measured from the subject. The biomarker of salivary cortisol comprises CpG dinucleotide methylation at one or more loci listed in Table 8. In certain embodiments, the sample is a blood, serum, or saliva sample.

In particular embodiments, the DNA methylation levels are measured using polymerase chain reaction (PCR). In certain embodiments, the PCR is quantitative PCR, real-time quantitative PCR, or nested PCR. In a further embodiment, the DNA methylation levels are further measured using a sequencing assay. In certain embodiments, the measurement of DNA methylation levels can be accomplished using a primer described herein including, for example, one or more of SEQ ID NOS:1-10. A skilled artisan can design similar primers based on the disclosure provided.

In the methods of the present invention, an area under the receiver operator characteristic curve analysis is used to predict or determining the risk of suicide attempt by the patient. In other embodiments, a linear discriminant analysis is used to predict or determining the risk of suicide attempt by the patient.

In particular embodiments, a prediction algorithm is used. In a specific embodiment, the prediction algorithm comprises a linear model. In a more specific embodiment, the prediction algorithm comprises a linear model with DNA methylation and rs7208505 genotype modeled with an interaction with stress or anxiety metric, controlling for age and sex as additive covariates. In certain embodiments, information as it pertains to early life trauma, perceived stress, or cortisol measurements can also be used as factors in a prediction model with the DNA methylation or genetic variation determine the risk of suicide ideation and/or attempt by the patient.

In a non-limiting embodiment, the linear model factors used to predict suicidal behavior comprise the following linear model coefficients: intercept: $4.817\times10-16$; rs7208505 DNA methylation: $-3.752\times10-17$; rs7208505 C/T genotype: $1.064\times10-15$; rs7208505 C/C genotype: $1.286\times10-15$, the stress/anxiety/cortisol/DNA methylation proxy of HPA axis function (termed stress component): $7.236\times10-1$; the rs7208505 DNA methylation X stress component interaction: $6.909\times10-2$; the rs7208505 C/T genotype x stress component interaction: $-3.851$; and rs7208505 C/C genotype x stress interaction: $-6.505$.

In another aspect, the present invention provides kits useful in the methods described herein. In one embodiment, a kit for determining suicide attempt risk in a subject comprises (a) a substrate for collecting a biological sample from the subject; and (b) means for measuring the DNA methylation levels of SNP rs7208505.

A scale representation of the SAT1 gene is depicted above the graph. D. A plot of the correlation coefficient with perceived stress in the prospective cohort (y axis) as a function of genomic coordinate for significantly associated CpGs. CpGs significantly associated with perceived stress are localized under an ENCODE GR binding peak, suggesting that stress, possibly influenced by SKA2 variation, may be an important modulator of SAT1 epigenetic variation in the region.

Figure 5:
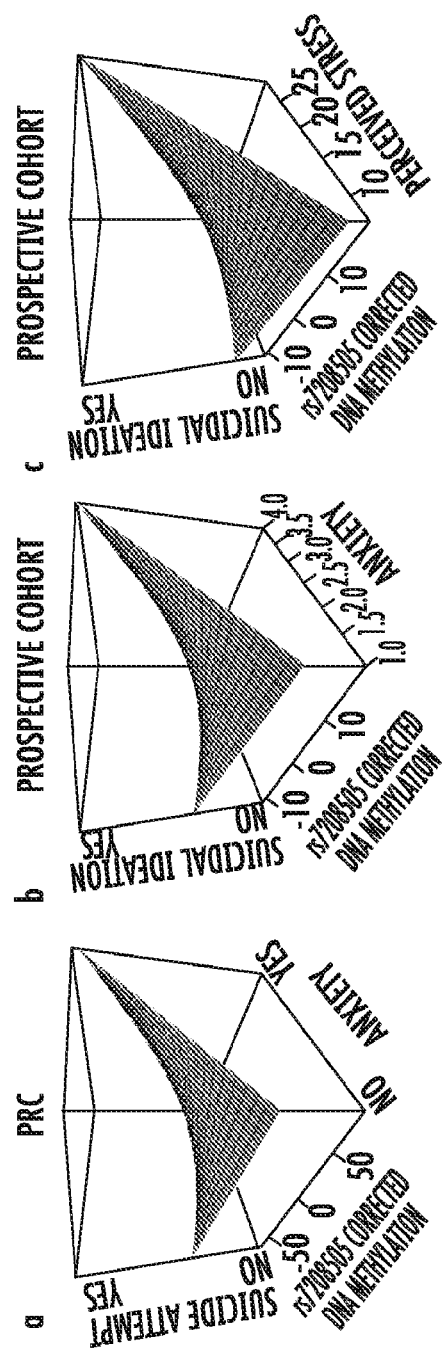

FIG. 5. Suicidal behavior prediction models. A. A three dimensional depiction of the effect of the rs7208505 genotype corrected SKA2 3'UTR DNA methylation (z axis) interaction with anxiety status (x axis) on suicide attempt in the PRC cohort (y axis) (F=1.4 7, df=315, p=0.16). B. A three dimensional depiction of the effect of the rs7208505 genotype corrected SKA2 3'UTR DNA methylation from first or second trimester blood (z axis) interaction with third trimester anxiety (x axis) on third trimester suicidal ideation in the prospective cohort (y axis) (F=8.1, df=18, p=1.2×10$^{-4}$). C. A three dimensional depiction of the effect of the rs7208505 genotype corrected SKA2 3'UTR DNA methylation from first or second trimester blood (z axis) interaction with third trimester perceived stress (x axis) on third trimester suicidal ideation in the prospective cohort (y axis) (F=0.33, df=19, p=5.6×10$^{-6}$).

Figure 6:
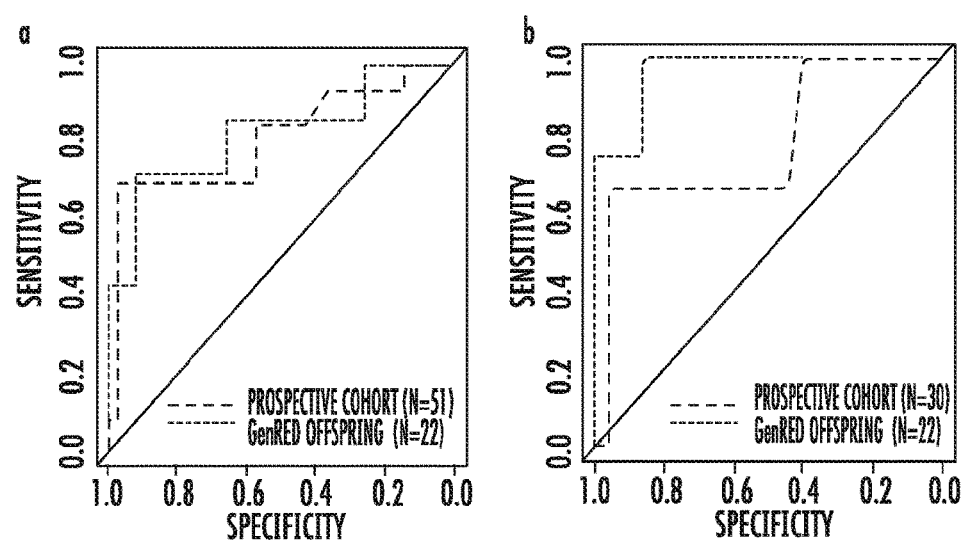

FIG. 6. Prediction of suicidal behavior. A. Receiver operator characteristic curves depicting the sensitivity (y axis) as a function of the specificity (x axis) for suicidal ideation predictions generated for the GenRED offspring and prospective cohorts based on models built on the PRC cohort data. B. ROC curves depicting the sensitivity (y axis) as a function of the specificity (x axis) for N=4 suicide attempt cases from the GenRED offspring cohort and those prospectively predicted third trimester suicidal ideation cases from the prospective cohort where blood was derived from first or second trimester blood.

Figure 7:
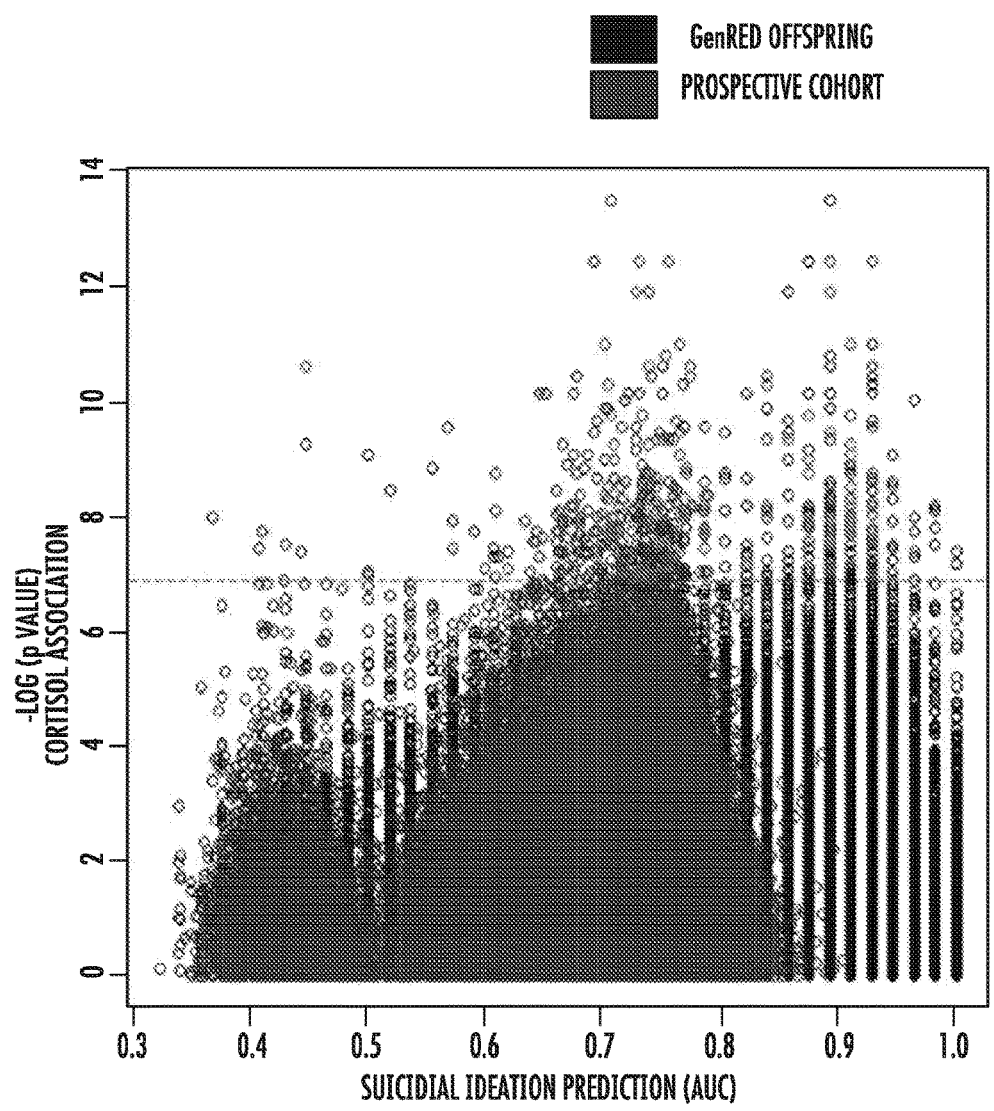

FIG. 7. Suicide prediction AUC as a function of cortisol association. Scatter plot of the—log of the p value of the association of salivary cortisol with DNA methylation (y axis) vs. the suicidal ideation prediction AUC (x axis) generated at each of the ~480,000 CpGs measured on the Illumina HM450 microarray. Data points above the dotted red line are those significantly associated with cortisol below a p value of 0.001. Red data points represent those selected as stress based proxies for use in the suicide prediction model and that appear in Table 7.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

As described herein, we employed a genome-wide scan for epigenetic alterations in post mortem tissues leading to the identification of a combined genetic and epigenetic association at rs7208505 located on the 3'UTR of the spindle and kinetochore associated complex subunit 2 (SKA2) gene. We demonstrate the functional relevance and show consistent associations of both epigenetic and genetic variation at this CpG across two brain cohorts and across one prospective and two retrospective peripheral blood cohorts. Finally, we demonstrate the predictive efficacy of statistical models generated at this locus for predicting suicidal ideation and suicide attempt across these cohorts.

I. Definitions

As used herein, the term "comparing" refers to making an assessment of how the methylation status, proportion, level or cellular localization of one or more biomarkers in a sample from a subject relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a subject is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a subject is the same as, more or less than, different from or otherwise corresponds (or not) to the methylation status, proportion, level, or cellular localization of predefined biomarker levels that correspond to, for example, a subject at risk for suicide attempt, not at risk for suicide attempt, and the like. In a specific embodiment, the term "comparing" refers to assessing whether the methylation level of one or more biomarkers of the present invention in a sample from a subject is the same as, more or less than, different from other otherwise correspond (or not) to methylation levels of the same biomarkers in a control sample (e.g., predefined levels that correlate to subject not at risk or predicted to attempt suicide).

As used herein, the terms "indicates" or "correlates" (or "indicating" or "correlating," or "indication" or "correlation," depending on the context) in reference to a parameter, e.g., a modulated proportion, level, or cellular localization in a sample from a subject, may mean that the subject is at risk for suicide attempt. In specific embodiments, the parameter may comprise the methylation status or level of one or more biomarkers of the present invention. A particular set or pattern of methylation of one or more biomarkers may indicate that a subject is at risk for suicide attempt (i.e., correlates to a subject at risk for suicide attempt). In other embodiments, a particular set or pattern of methylation of one or more biomarkers may be correlated to a subject being unaffected or not at risk of suicide attempt. In certain embodiments, "indicating," or "correlating," as used according to the present invention, may be by any linear or non-linear method of quantifying the relationship between methylation levels of biomarkers to a standard, control or comparative value for the prediction of suicide attempt, assessment of efficacy of clinical treatment, identification of a subject that may respond to a particular treatment regime or pharmaceutical agent, monitoring of the progress of treatment, and in the context of a screening assay, for the identification of an anti-suicide attempt therapeutic.

The terms "subject," "individual," or "patient" are used interchangeably herein, and refer to a mammal, particularly, a human. The subject may have mild, intermediate or severe disease. The subject may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a subject sample and/or detecting the methylation status or level of a biomarker(s) in a sample. In one embodiment, the terms refer to obtaining a subject sample and detecting the methylation status or level of one or more biomarkers in the sample. In another embodiment, the terms "measuring" and "determining" mean detecting the methylation status or level of one or more biomarkers in a subject sample. Measuring can be accomplished by methods known in the art and those further described herein including, but not limited to, quantitative polymerase chain reaction (PCR). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a subject over time.

In particular embodiments, a biomarker would be unmethylated in a normal sample (e.g., normal or control tissue, or normal or control body fluid, stool, blood, serum, amniotic fluid), most importantly in healthy stool, blood, serum, amniotic fluid or other body fluid. In other embodiments, a biomarker would be hypermethylated in a sample from a subject having or at risk of suicide attempt, preferably at a methylation frequency of at least about 10%, at least about 20%, at least about 30%, at least about 40%, at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including SKA2. In more specific embodiments, a methylation profile refers to the methylation states of the 3' untranslated region (UTR) of SKA2. In even more specific embodiments, a methylation profile refers to the methylation state of CpG located on the minus strand of chromosome 17, position 57287729.

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. This is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) NUCLEIC ACIDS RES. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pm1 I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "subject sample," "biological sample," and the like, encompass a variety of sample types obtained from a patient, individual, or subject and can be used in a diagnostic or monitoring assay. The subject sample may be obtained from a healthy subject, a subject suspected to be at risk for suicide attempt (family history) or a subject having a conditions associated with suicide attempt (e.g., depression, bipolar disorder, and the like). Moreover, a sample obtained from a subject can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or subject, e.g., a control or normal cell, organ, or subject, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a suicide attempt treatment (or treatment for a condition that may lead to suicide attempt (e.g., depression)) on a subject. In yet another embodiment, a transcription rate, mRNA level, translation rate, protein level, biological activity, cellular characteristic or property, genotype, phenotype, etc. can be determined prior to, during, or after administering a therapy into a cell, organ, or subject. In a further embodiment, a "suitable control" or "appropriate control" is a predefined value, level, feature, characteristic, property, etc. A "suitable control" can be a methylation profile of one or more biomarkers of the present invention that correlates to suicide attempt, to which a subject sample can be compared. The subject sample can also be compared to a negative control, i.e., a methylation profile that correlates to not at risk of suicide attempt.

II. Hypermethylated Biomarkers and Detection Thereof

The biomarkers of the present invention are differentially methylated in subjects at risk of suicide attempt versus "normal" individuals. Such biomarkers can be used individually as diagnostic tool, or in combination as a biomarker panel. In particular embodiments, the biomarkers include SKA2. In more specific embodiments, the biomarkers comprise the 3'UTR region SKA2. In even more specific embodiments, the biomarkers comprise CpG located on the minus strand of chromosome 17, position 57187729. The sequence of this biomarker is publicly available. Other biomarkers may include ATP8A1, LOC153328, and KCNAB2.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition.

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., suicide attempt) and thus diagnose risk or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. Alternatively, the method can encompass amplifying intact DNA after restriction enzyme digestion, thereby only amplifying DNA that was not cleaved by the restriction enzyme in the area amplified. See, e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., DeGraves, et al., 34(1) BIOTECHNIQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See, e.g., Xiong & Laird, 25 NUCLEIC ACIDS RES. 2532-34 (1997); and Sadri & Hornsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331, 393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

III. Determination of a Subject's Risk of Suicide Attempt/Ideation

The present invention relates to the use of biomarkers to predict suicide attempt and/or ideation. More specifically, the biomarkers of the present invention can be used in diagnostic tests to determine the risk of or predict suicide attempt in an individual, subject or patient. More specifically, the biomarkers to be detected in predicting suicide risk include SKA2, ATP8A1, LOC153328, and KCNAB2. Other biomarkers known in the relevant art may be used in combination with the biomarker described herein including, but not limited to, the assessment of levels of stress hormones and their metabolites, questionnaires such as the Columbia-Suicide Severity Rating Scale, salivary cortisol levels, gene expression measures, or genetic variation deemed predictive of suicide attempt.

A. Biomarker Panels

The biomarkers of the present invention can be used in diagnostic tests to assess, determine, and/or qualify (used interchangeably herein) suicide ideation/attempt risk in a subject. The phrases "at risk of suicide ideation/attempt," "predictive of suicide ideation/attempt" and the like include any distinguishable manifestation of the risk or associated condition, including non-risk. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker of the present invention may show a statistical difference in different suicide attempt risks of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and individuals at risk of suicide attempt. In certain embodiments, the biomarkers are measured in a subject sample using the methods described herein and compared, for example, to predefined biomarker levels and correlated to suicide attempt risk. In particular embodiments, the measurement(s) may then be compared with a relevant diagnostic amount(s), cut-off(s), or multivariate model scores that distinguish a positive suicide attempt risk status from a negative suicide attempt risk status. The diagnostic amount(s) represents a measured amount of a hypermethylated biomarker(s) above which or below which a subject is classified as having a particular suicide attempt risk status. For example, if the biomarker(s) is/are hypermethylated compared to normal, then a measured amount(s) above the diagnostic cutoff(s) provides a diagnosis of suicide attempt risk. Alternatively, if the biomarker(s) is/are hypomethylated in a subject, then a measured amount(s) at or below the diagnostic cutoff(s) provides a diagnosis of non-suicide attempt risk. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from subjects with the different suicide attempt risk statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to predict suicide attempt, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al.,12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Suicide Ideation/Attempt

In a specific embodiment, the present invention provides methods for determining the risk of suicide attempt by a subject. Biomarker methylation percentages, amounts or patterns are characteristic of various risk states, e.g., high, medium or low. The risk of suicide attempt is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Subject Management

In certain embodiments of the methods of the present invention, the methods further comprise managing subject treatment based on the biomarker methylation status. Such management includes the actions of the physician or clinician subsequent to determining suicide attempt risk status. For example, if a physician makes a prognosis of suicide attempt, then a certain regime of monitoring would follow. An assessment of the risk using the methods of the present invention may then require a certain therapy regimen. Alternatively, a diagnosis of non-risk of suicide attempt might be followed with further testing to determine a specific disease that the subject might be suffering from. Also, further tests may be called for if the test gives an inconclusive result on suicide attempt risk status.

D. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a subject on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-suicide attempt risk profile. Therefore, one can follow the course of the methylation status of one or more biomarkers in the subject during the course of treatment. Accordingly, this method involves measuring methylation levels of one or more biomarkers in a subject receiving drug therapy, and correlating the levels with the suicide attempt risk status of the subject (e.g., by comparison to predefined methylation levels of the biomarkers that correspond to different suicide attempt risk statuses). One embodiment of this method involves determining the methylation levels of one or more biomarkers at at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward suicide attempt risk indications.

E. Generation of Classification Algorithms for Qualifying Suicide Ideation/Attempt Risk In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition or risk of suicide attempt.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002/0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

F. Kits for the Detection of Suicide Ideation/Attempt Biomarkers

In another aspect, the present invention provides kits for qualifying suicide attempt risk status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfite, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including SKA2. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including SKA2.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including SKA2.

In some embodiments, the kits comprise a methylation binding moiety and one or more polynucleotides to quantify the number of copies of at least a portion of a DNA region of a biomarker of the present invention including SKA2. A methylation binding moiety refers to a molecule (e.g., a polypeptide) that specifically binds to methyl-cytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Human Samples. The samples obtained for this project consisted of post mortem frontal cortical tissue and peripheral blood samples from two and three cohorts, respectively. Brain tissue was obtained from the NICHD Brain Bank of Developmental Disorders as described previously[27] and the Stanley Medical Research Foundation microarray collection. Peripheral blood was obtained from the GenRED Offspring study, a prospective postpartum depression study described previously[53], and a subset of a prospective study conducted in the context of an epidemiologically-based group-randomized prevention trial called the PRC sample[65] who consented to blood draw. Relevant demographic information for this project appears in Table 1.

TABLE 1

Sample demographics

| | | Post Mortem Brain Samples | | | | | | | |
|---|---|---|---|---|---|---|---|---|---|
| Cohort | Diagnosis | Suicidal Behavior (yes:no) | N | Age | Age (sd) | Sex (M:F) | Substance Use (yes:no) | Psychiatric Medication (yes:no) | PMI | PMI (sd) |
| NICHD | Major depression | 21:08 | 29 | 32.00 | 15.92 | 14:15 | 9:20 | 12:17 | 18.10 | 7.09 |
| | Control | 2:27 | 29 | 32.10 | 16.05 | 14:15 | 2:27 | 0:29 | 16.14 | 4.97 |

TABLE 1-continued

Sample demographics

| | | | | | | | | | | |
|---|---|---|---|---|---|---|---|---|---|---|
| SMRI | Bipolar disorder | 13:15 | 28 | 46.14 | 11.09 | 13:15 | 24:3 | 27:1 | 39.21 | 19.7 |
| | Control | 0:29 | 29 | 43.76 | 7.73 | 22:07 | 16:13 | 0:29 | 29.10 | 13.7 |
| | Schizophrenia | 6:23 | 29 | 43.07 | 6.58 | 22:07 | 19:08 | 29:0 | 31.86 | 16.1 |
| McL | Bipolar disorder | 4:08 | 12 | 60.50 | 20.01 | 7:05 | 1:11 | 8:04 | 21.07 | 10.5 |
| | Control | 0:12 | 12 | 61.67 | 16.22 | 8:04 | 4:08 | 0:12 | 21.33 | 5.67 |

Peripheral Blood Samples

| Cohort | Diagnosis | Suicidal Behavior (yes:no) | N | Age | Age (sd) | Sex (M:F) | Substance Use (yes:no) | Psychiatric Medication (yes:no) |
|---|---|---|---|---|---|---|---|---|
| GenRED Offspring Suicidal Ideation | Bipolar disorder | 1:0 | 1 | 21 | NA | 0:1 | 1:00 | 0:1 |
| | Major depression | 3:5 | 8 | 18.13 | 3.04 | 6:02 | 2:06 | 1:7 |
| | Control | 3:10 | 13 | 15.31 | 2.32 | 5:08 | 0:13 | 4:09 |
| GenRED Offspring Suicide Attempt | Bipolar disorder | 1:0 | 1 | 21 | NA | 0:1 | 1:00 | 0:1 |
| | Major depression | 2:6 | 8 | 18.13 | 3.04 | 6:02 | 2:06 | 1:7 |
| | Control | 1:12 | 13 | 15.31 | 2.32 | 5:08 | 0:13 | 4:09 |
| Prospective Suicidal Ideation | Bipolar disorder | 3:11 | 14 | 29.29 | 6.39 | 0:14 | 1:13 | 7:6 |
| | Major depression | 10:27 | 37 | 31.45 | 6.38 | 0:38 | 1:37 | 26:12 |
| PRC | Major depression | 20:10 | 30 | 29.64 | 1.21 | 11:19 | 17:13 | NA |
| | Control | 59:236 | 295 | 30.46 | 2.56 | 117:178 | 70:225 | NA |
| | Major depression | 15:15 | 30 | 29.64 | 1.21 | 11:19 | 17:13 | NA |
| | Control | 33:262 | 295 | 30.46 | 2.56 | 117:178 | 70:225 | NA |

NICHD cohort. A cohort of post mortem frontal cortical samples with MDD and matched controls was obtained from the NICHD University of Maryland Brain Bank of Developmental Disorders. Approximately 21% of the sample was African American, 78% was Caucasian, and 1% was Asian.

SMRI cohort. A cohort of post mortem prefrontal cortical samples with BPD, SZC, and matched controls was obtained from the Stanley Medical Research Institute. Approximately 1% of the sample was African American, 1% was Hispanic, 1% was Native American, and 97% was Caucasian.

McL cohort: A cohort of post mortem prefrontal cortical samples with bipolar disorder and matched controls was obtained from the Harvard Brain Bank at McLean Hospital. 100% of the sample was Caucasian.

GenRED Offspring Study. Adolescent and young adult offspring were ascertained through probands available from the Johns Hopkins and University of Iowa sites of the Genetics of Recurrent Early Onset Depression Study.[66,67] Probands were characterized using the Diagnostic Interview for Genetic Studies (DIGS)[68] and the FIGS (Family Instrument for Genetic Studies)[69] and received a best-estimate diagnosis of recurring MDD with at least two lifetime major depressive episodes, onset before age 31 (or a single episode of major depression that lasted three years and began before age 31), at least one sibling or parent with recurrent MDD with onset before age 41, MDD independent of substance dependence (that is, no lifetime dependence, MDD before dependence, or MDD after at least two years of remission from dependence), no diagnosis of bipolar or schizoaffective disorder or schizophrenia, and no suspected bipolar-I disorder in a parent or sibling. GenRED I and II participants were approached for the offspring study between October 2009 and August 2013. All offspring in the 12-21 age range were invited to participate by being interviewed (with the K-SADS) and providing serial cortisol samples at waking, 30 minutes after waking and 60 minutes after waking on a weekday and a weekend day as well as a blood specimen for DNA methylation studies. Only those offspring who provided blood samples were included in this study. At least one parent had to be available for an interview about all of their participating offspring (with the Kiddie Schedule for Affective Disorders (K-SADS).[70] IQ in offspring was not formally tested, but each subject was required to be able to complete the interview and the individual questionnaires as part of the study protocol. Offspring with brain disease, schizophrenia, mental retardation and those taking glucocorticoids (e.g., prednisone for asthma) were not included. Informed consent (or assent with parental consent, for subjects<18) was obtained after a thorough explanation of the study. All clinical procedures were approved by institutional review boards at the Johns Hopkins School of Medicine and the University of Iowa, School of Medicine.

Johns Hopkins Center for Prevention Research Study. Data are from a prospective study conducted in the context of an epidemiologically-based group-randomized prevention trial.[65,71] In brief, the trial recruited two successive cohorts of students [1196 from Cohort 1 in 1985 and 1115 from Cohort 2 in 1986] as they entered first grade in 19 elementary schools in Baltimore, Md. (49.8% male and 67.1% ethnic minority consistent with the population in Baltimore City schools). Since 1985, participants have been assessed through middle school, twice in young adulthood, and most recently when participants were 30-32 years old. Data for this study were derived from blood collected at the age 30-32 year follow-up wave. DNA methylation analyses were restricted to the 328 individuals participating in the age 30-32 wave who at the time of this analysis provided a blood sample (60% female and 76% African American, lacking another 12 who provided blood later). Attrition in the cohort was slightly greater among males and whites (p<.01). Standardized assessments were conducted by trained non-clinical interviewers with the most recent wave collected via a computerized interview that was conducted by the interviewer, and, when assessing potentially sensitive topics such as drug involvement, conducted by the respondent using the computer). This study was approved by the Institutional Review Board at Johns Hopkins University. All participants provided informed consent to participate.

Prospective sample. We recruited 93 pregnant women with a history of either Major Depression or Bipolar Disorder (I, II or NOS) and prospectively followed them during pregnancy and after delivery in order to identify genetic and clinical characteristics that precede the development of a postpartum depressive episode. The average age of the participants was 30.6 and 70% of the sample was Caucasian. Participants were managed by their treating psychiatrist as clinically indicated and were evaluated during each trimester of pregnancy and then 1 week, 1 month and 3 months postpartum. Women were classified as being depressed if they met DSM-IV criteria for a Major Depressive Episode (MDE) based on a psychiatric interview at each time point (first, second, and third trimester and 1 week and 1 month postpartum). Suicidal ideation was assessed from the Montgomery Asberg Depression Rating Scale (MADRS) question 10 and from the Inventory of Depressive Symptomology-Self Report (IDS-SR) question 18 at each time point.

Illumina DNA methylation profiling. Samples quality assessment and microarray analysis were conducted at The Sidney Kimmel Cancer Center Microarray Core Facility (Baltimore, Md., USA) at Johns Hopkins University using Illumina's Infinium Human Methylation450 Beadchip Kit (WG-314-1001) according to the manufacturer's manual. Images were processed in Illumina's iScan scanner and data were extracted using Methylation Module of GenomeStudio v1.0 Software. Illumina probe type was corrected using the Beta2M function in the wateRmelon package in R. Methylation status of each CpG site was calculated as β (beta) value based on following definition:

β value=(signal intensity of methylation-detection probe)/(signal intensity of methylation-detection probe±signal intensity of non-methylation-detection probe±100).

Genome-wide DNA methylation data were obtained from Illumina HM450 microarrays previously generated by our group' for which data is located under Gene Expression Omnibus accession: GSE15745. A discovery set of NICHD prefrontal cortical tissue data was generated from N=10 Caucasian individuals with Major Depression who did (N=7) and did not (N=3) die by suicide for whom bulk tissue data was available. A replication set consisted of the remaining N=8 suicide and N=4 non-suicide samples from Caucasians with Major Depression in the NICHD cohort not originally interrogated.

Sodium Bisulfite Pyrosequencing. Bisulfite conversion was carried out using EZ DNA Methylation Gold Kit (Zymo Research, Irvine, Calif., USA) according to the manufacturer's instructions. Nested PCR amplifications were performed with a standard PCR protocol in 25 ml volume reactions containing 3-4 µl of sodium-bisulfite-treated DNA, 0.2 uM primers, and master mix containing Taq DNA polymerase (Sigma-Aldrich, St. Louis, Mo., USA). Primer sequences for the SKA2 3'UTR CpG and those two CpGs analyzed upstream can be found included:

TABLE 2

SKA2 pyrosequencing primer sequences

| | Primer Name | Primer Sequence 5'-3' |
|---|---|---|
| SKA2 3'UTR | SKA2_Forward Outside SKA2_Fo | GAGAAATAAGTTATATTTTAGTATTAGATA (SEQ ID NO: 1) |
| | SKA2_Reverse Outside SKA2_Ro | AAAATAATACAATCTAATTTTTCTCCCT (SEQ ID NO: 2) |
| | SKA2_Forward Inside SKA2_Fib | biotin-GAGATGGTTTTGGGATGTGATG (SEQ ID NO: 3) |
| | SKA2_Reverse Inside SKA2_Ri | TAACTAAAAACAAAACCACTTTTAATACTA (SEQ ID NO: 4) |
| | SKA2_Pyrosequencing Primer SKA2_Pyro | ATTATAATCTCTCCATAATACTACC (SEQ ID NO: 5) |
| SKA2_upstream | SKA2_upstream_Forward Outside SKA2_upstream_Fo | AATTGTTTTGTTTAGTTTGAATATTTTAAG (SEQ ID NO: 6) |
| | SKA2_upstream_Reverse Outside SKA2_upstream_Ro | TATCTAATACTAAAATATAACTTATTTCTC (SEQ ID NO: 7) |
| | SKA2_upstream_Forward Inside SKA2_upstream_Fib | TGTTTAGGTTGGAATGTAGTGGTA (SEQ ID NO: 8) |
| | SKA2_upstream_Reverse Inside SKA2_upstream_Ri | CCTAATCAAAATAATAAAACCCCATC (SEQ ID NO: 9) |
| | SKA2_upstream_Pyrosequencing Primer SKA2_upstream_Pyro | CTCTACTAAAAATACAAAAAAATAACC (SEQ ID NO: 10) |

PCR amplicons were processed for pyrosequencing analysis according to the manufacturer's standard protocol (Qiagen, Gaithersburg, Md., USA) using a PyroMark MD system (Qiagen) with Pyro Q-CpG 1.0.9 software (Qiagen) for CpG methylation quantification. Only those data values receiving a "Pass" value or "Check" were considered for downstream analysis. "Check" signals were accepted only in the case of failed reference sequence patterns upstream of the CpG of interest involving failure of the pyrosequencing chemistry to properly account for long runs of thymines. All data incorporated into analyses demonstrated proper bisulfate conversion based on internal pyrosequencing assay checks of cytosines not located within CpG dinucleotides.

Salivary Cortisol. Salivary cortisol samples were taken at 0, 30, and 60 minutes after weekend waking. Saliva was separated from Salimetrics (State College, Pa.) oral swabs by centrifugation and submitted to the Center for Interdisciplinary Salivary Bioscience Research at Johns Hopkins (Baltimore, Md.) for salivary cortisol measurement. Cortisol measurements were determined by sandwich ELISA assay using the Salivary Cortisol Enzyme ImmunoAssay Kit (Salimetrics) according to the manufacturer's instructions. A single cortisol metric was generated per individual by calculating the AUC from the three time point measurements.

Cell Culture. Human SH-Sy5y neuroblastoma cell lines were cultured using DMEM (Invitrogen, Carlsbad, Calif.) supplemented with 10% fetal bovine serum (Hyclone, Logan, Utah) and 1% penicillin/streptomycin/neomycin (Invitrogen) under standard conditions (5% $CO_2$, 37 C). Six replicate wells per experimental treatment were performed. Cells were quantified on a hemocytometer and between $5 \times 10^6$ and $1 \times 10^7$ cells plated per well depending on treatment duration. Cells were treated with dexamethasone at a concentration of 100 uM for 1 week, 24 hours, 1 hour, and 1 hour followed by removal of treatment media and replacement with standard media for 24 hours prior to cell division.

Quantitative Real Time PCR. All SKA2 gene expression data and rs7208505 genotyping was performed using quantitative real time PCR (RT-qPCR). The exception was for the SMRI cohort, which was downloaded from the Stanley Genomics Database at www.stanleygenomics.org. Genotype calls for rs7208505 were obtained from Study 20. For SKA2 hippocampal gene expression, fRMA values from HGU133_Plus_2 microarray probes 225684_at and 225684_at were obtained from Study 17 and averaged. Genotyping of rs7208505 was performed on genomic DNA using a Life Technologies Taqman assay for rs7208505 (C_23546_20). For gene expression, mRNA was extracted from brain tissue using the RNeasy Lipid and Tissue kit (Qiagen) and from tissue culture using the RNeasy Mini kit (Qiagen) according to the manufacturer's protocols followed by RNA quality assessment through visualization following electrophoresis. Reverse transcription was carried out using a combination of oligo DT and random primers using the Quantitect Reverse Transcription kit (Qiagen), according to the manufacturer's protocol. Quantitative real-time PCR was performed on an ABI 7900HT Fast Real-Time PCR system to assess steady state mRNA levels. ABI Taqman probes (Life Technologies, Carlsbad, Calif.) were obtained from the manufacturer's website. Assays for SKA2 (hs00735057_m1) were run in triplicate alongside a reference gene, β-actin (Hs03023943_g1), and average relative gene expression of gene-specific transcripts selected was quantified using the delta CT method. To determine relative expression values, the $-\Delta\Delta Ct$ method (Applied Biosystems) was used, where triplicate Ct values for each sample were averaged and subtracted from those derived from the housekeeping gene ACTB. The Ct difference for a calibrator sample was subtracted from those of the test samples, and the resulting $-\Delta\Delta Ct$ values were raised to a power of 2 to determine normalized relative expression Study Metrics. Suicidal ideation, anxiety, and stress metrics were obtained through different scales per cohort. For the GenRED offspring cohort, suicidal ideation and suicide attempt were derived from the Composite International Diagnostic Interview (CIDI) Suicidality Questionnaire. A positive anxiety metric was determined by a score of ≥25 on the Self-Report for Childhood Anxiety Related Disorders (SCARED)[2]. For the prospective cohort, suicidal ideation was measured by numeric responses to question 10 of the Montgomery Asberg Depression Rating Scale (MADRS), anxiety was measured by numeric responses to question 4 of the Edinburgh Postnatal Depression Scale (EPDS)[3], and perceived stress was measured by the total of the Perceived Stress Scale (PSS)[4]. For prospective sample receiver operator characteristic curve predictions, suicidal ideation metrics were converted to a binary format by reducing quantitative scores of greater than zero to one. A more stringent suicidal ideation classification was also tested by classifying only those suicidal ideation scores greater than or equal to two as a positive suicidal ideation status for evaluation of predictive accuracy. For the PRC cohort, all metrics were derived as responses to a standardized interview.[5,6] Suicidal ideation was measured as a binary response to the question: Have you ever felt so low you thought of committing suicide?; suicide attempt was measured as a binary response to the question: Have you ever attempted suicide?; anxiety was measured as a binary response to the question: Do you consider yourself a nervous person? Following an affirmative response to the suicide attempt question, intent to die was measured as a binary response to the question: Did you intent to die?

Statistical Analysis. Unless otherwise stated, reported statistics derive from linear regression analysis, adjusted for age, sex, race, and post mortem interval (in brain cohorts) generated in R(http://www.r-project.org/). Relevant additional covariates were adjusted for if their inclusion into the model as an additive covariate caused the beta value to change by greater than 15%. Using the Cramer-von Mises test, all data distributions that rejected the null hypothesis of normality were subsequently evaluated with non-parametric tests. All statistical tests were two tailed, p<0.05 denotes statistical significance, and ±denotes the standard deviation. Microarray analysis employed False Discovery Rate correction for multiple testing. Where specified, genotype correction of SKA2 3'UTR DNA methylation was achieved by taking the residuals of a linear model of SKA2 3'UTR DNA methylation as a function of rs7208505 genotype. Randomization was employed within all experimental processing batches. Personnel performing laboratory experiments were blind to caseness.

Weighted Genome Co-expression Network Analysis. Weighted Genome Co-expression Network Analysis (WGCNA)[34] was performed using the WGCNA package in R. For neuronal and glial analyses, respectively, 9784 and 16,644 nominally significant loci from the NICHD neuronal and glial DNA specific HM450 microarray datasets were used for correlation with a power of 6 and minimum module size of 5.

Study metrics. Suicidal ideation, anxiety, and stress metrics were obtained through different scales per cohort. For the GenRED offspring cohort, suicidal ideation and suicide attempt were derived from the Composite International Diagnostic Interview (CIDI) Suicidality Questionnaire. A positive anxiety metric was determined by a score of ≥25 on the Self-Report for Childhood Anxiety Related Disorders (SCARED). For the prospective cohort, suicidal ideation was measured by numeric responses to question 10 of the Montgomery Asberg Depression Rating Scale (MADRS), anxiety was measured by numeric responses to question 4 of the Edinburgh Postnatal Depression Scale (EPDS), and perceived stress was measured by the total of the Perceived Stress Scale (PSS). For prospective sample receiver operator characteristic curve predictions, suicidal ideation metrics were converted to a binary format by reducing quantitative scores of greater than zero to one. A more stringent suicidal ideation classification was also tested by classifying only those suicidal ideation scores greater than or equal to two as a positive suicidal ideation status for evaluation of predictive accuracy. For the PRC cohort, all metrics were derived as responses to a standardized interview. Suicidal ideation was measured as a binary response to the question: Have you ever felt so low you thought of committing suicide?; suicide attempt was measured as a binary response to the question: Have you ever attempted suicide?; anxiety was measured as a binary response to the question: Do you consider yourself a nervous person? Following an affirmative response to the suicide attempt question, intent to die was measured as a binary response to the question: Did you intend to die?

MADRS suicidal ideation question: Numeric metric example: Question 10. Suicidal thoughts. Representing the feeling that life is not worth living, that a natural death would be welcome, suicidal thoughts, and preparations for suicide. Suicide attempts should not in themselves influence the rating. 0=Enjoys life or takes it as it comes. 2=Weary of life. Only fleeting suicidal thoughts. 4=Probably better off dead. Suicidal thoughts are common, and suicide is considered as a possible solution, but without specific plans or intention. 6=Explicit plans for suicide when there is an opportunity. Active preparations for suicide.

Results

Figure 1:
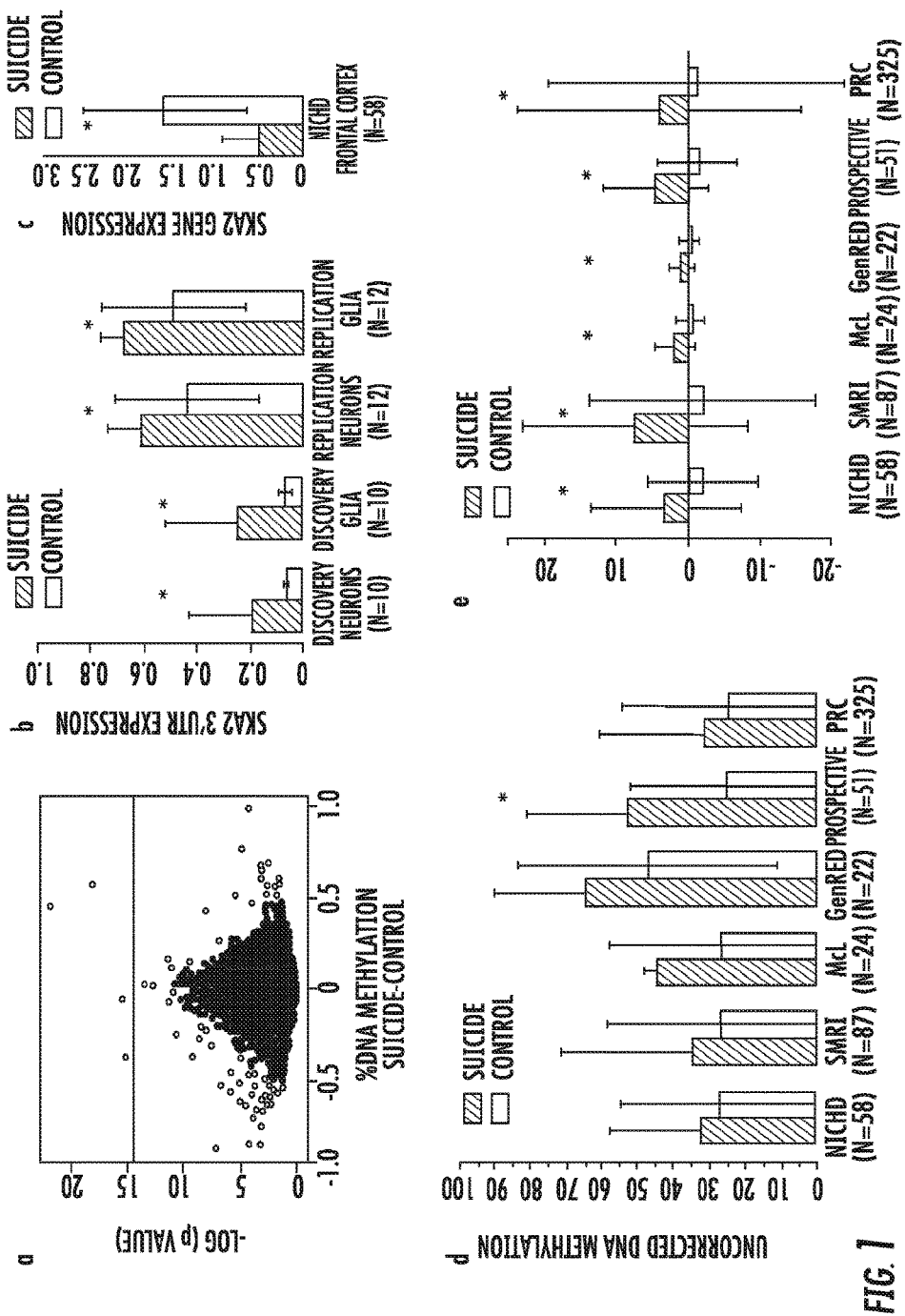
FIG. 1. SKA2 discovery and functional analysis. A. Volcano plot of linear model based DNA methylation differences (x axis) and negative natural log of the p value (y axis) generated for N=7 suicide and N=3 non-suicide Major Depression National Institute of Child Health and Development (NICHD samples) generated in bulk tissue. False Discovery Rate: significant loci appear above the dashed line identifying significant hits at ATP8A1(F=3424.53, df=6, p=$3.2\times10^{-10}$), SKA2 (F=1101.663, df=6, p=$1.3\times10^{-8}$), LOC153328 (F=384.31, df=6, p=$2.5\times10^{-7}$), and KCNAB2 (F=243.51, df=6, p=$2.09\times10^{-7}$). B. Bar graph depicting significant differences in DNA methylation for the cg13989295 Illumina probe within the SKA2 3'UTR for the discovery sample neurons (F=784, df=6, p=$2.76\times10^{-8}$), discovery sample glia (F=421, df=6, p=$1.82\times10^{-7}$), replication neurons (F=2.2, df=8, p=0.04) and replication sample glia (F=3.2, df=8, p=0.0163). Large error bars derive from unaccounted for variation in rs7208505 genotype. C. Bar graph depicting significant differences in SKA2 gene expression for N=23 suicide and N=35 controls from prefrontal cortical samples from the NICHD cohort (Wilcoxon Rank Sum test; W=97, df=49.91, p=$3.8\times10^{-06}$). D. Bar graph depicting uncorrected DNA methylation levels at rs7208505 (y axis) across all cohorts included in the study (x axis). E. Bar graph depicting genotype corrected DNA methylation levels at rs7208505 (y axis) across all cohorts included in the study (x axis). Associated significance metrics are located in Table 2. All error bars represent standard deviations. *P≤0.05.

Microarray Analysis. We performed a genome-wide screen for DNA methylation variation associated with suicide in a small discovery sample of post mortem prefrontal cortical tissue from the NICHD sample. Using a linear model adjusting for age and sex as covariates, we identified four loci significantly associated with suicide after correction for multiple testing corresponding to the ATP8A1 (cg24533989), SKA2 (cg13989295), LOC153328 (cg15918259), and KCNAB2 (cg17106415) genes (FIG. 1A). Using fluorescence activated cell sorting (FACS), we separated neuronal and glial nuclei as described previously[1], after which only SKA2 exhibited nominal significance in the neuronal and glial fractions of both the discovery and replication sets (FIG. 1B). The identified CpG is located on the antisense strand of chromosome 17 at position 57187729 (hg19) within the 3'UTR of the SKA2 (spindle and kinetochore associated complex subunit 2) gene which encodes a scaffold protein implicated in chaperoning the glucocordicoid receptor (GR) into the nucleus[7]. Importantly, the cytosine (C) at this position represents the alternative allele of SNP, rs7208505, while the reference allele is a thymine (T). Importantly, T allele abrogates the CpG dinucleotide and cannot be methylated. The assessment of rs7208505 epigenetic and genetic variation in an additive linear model demonstrated significant associations of both model terms with suicide across the entire NICHD cohort of N=23 suicide cases and N=35 controls independent of ethnicity or DSM-IV diagnosis (Table 3). These associations replicated in two independent cohorts of post mortem prefrontal cortical samples from the Stanley Medical Research Institute (SMRI) cohort and the Harvard Brain Bank at McLean Hospital (McL) cohort (FIG. 1E, Table 3) and did not appear to be related to the mode of death.

TABLE 3

SKA2 rs7208505 epigenetic and genetic effects on suicide risk

| | Brain | | | | | | | | |
|---|---|---|---|---|---|---|---|---|---|
| | NICHD Neurons Suicide (N = 58) | | | SMRI Brain Suicide (N = 87) | | | McL Brain Suicide (N = 24) | | |
| Model Terms | β value | Error | P value | β value | Error | P value | β value | Error | P value |
| DNA methylation | 0.015 | 0.0067 | 0.026 | 0.0063 | 0.0026 | 0.018 | 0.085 | 0.022 | 0.0014 |
| rs7208505 C/T | −0.58 | 0.27 | 0.037 | −0.3 | 0.13 | 0.027 | −3.4 | 0.96 | 0.0026 |
| rs7208505 C/C | −1.5 | 0.57 | 0.014 | −0.47 | 0.22 | 0.037 | −7.1 | 1.9 | 0.0014 |
| Age | −0.01 | 0.0041 | 0.019 | −0.0039 | 0.0051 | 0.44 | −0.014 | 0.003 | 0.00018 |
| Sex | −0.08 | 0.13 | 0.54 | 0.17 | 0.094 | 0.068 | 0.035 | 0.11 | 0.75 |
| PMI | 0.019 | 0.011 | 0.084 | 0.0037 | 0.0027 | 0.17 | −0.0071 | 0.0075 | 0.35 |
| F | 2.2 | | | 2.4 | | | 8.3 | | |
| DF | 48 | | | 75 | | | 17 | | |
| Model R² | 0.27 | | 0.042 | 0.24 | | 0.017 | 0.75 | | 2.6 × 10⁻⁴ |

| | Blood | | | | | | | | |
|---|---|---|---|---|---|---|---|---|---|
| | GenRED offspring Suicidal Ideation (N = 22) | | | Prospective Suicidal Ideation (N = 51) | | | PRC Suicidal Ideation (N = 325) | | |
| Model Terms | β value | Error | P value | β value | Error | Pvalue | β value | Error | P value |
| DNA methylation | 0.17 | 0.074 | 0.043 | 0.071 | 0.02 | 0.00075 | 0.0023 | 0.0011 | 0.043 |
| rs7208505 C/T | −6.5 | 3.1 | 0.056 | −3 | 1 | 0.0046 | −0.051 | 0.06 | 0.4 |
| rs7208505 C/C | −15 | 6.7 | 0.047 | −6.1 | 1.8 | 0.0016 | −0.14 | 0.1 | 0.16 |
| Age | 0.033 | 0.039 | 0.41 | 0.018 | 0.021 | 0.41 | 0.0061 | 0.0093 | 0.51 |
| Sex | −0.087 | 0.21 | 0.69 | na | na | na | −0.0016 | 0.047 | 0.97 |
| F | 2 | | | 2.7 | | | 3.9 | | |
| DF | 12 | | | 42 | | | 314 | | |
| Model R² | 0.5 | | 0.14 | 0.34 | | 0.018 | 0.11 | | 6.1 × 10⁻⁵ |

DNAm = DNA methylation;
C/T = rs7208505 heterozygotes;
C/C = rs7208505 alternative homozygotes We investigated the association of rs7208505 corrected DNA methylation with the method of death in suicide decedents in all post mortem brain cohorts in efforts to assess if suicide associated DNA methylation increases at SKA2 are the result of the process of dying.

Methods of death were classified into those involving asphyxiation, including hanging and drowning, overdose, violent means, and unknown method. No significant differences were observed across groups in a combined analysis of all three brain cohorts (ANOVA, F=0.53, df=3, p=0.66). Results were similar when performed for each cohort separately (ANOVA, NICHD, F=0.59, df=3, p=0.63 ; SMRI, F=0.26, df=2, p=0.77; McL F=1.25, df=2, p=0.53).

Gene expression and functional relevance of the identified locus. In the NICHD brain cohort, SKA2 exhibited significantly lower gene expression values in suicide cases as compared to controls (FIG. 1C). SKA2 expression was significantly negatively associated with DNA methylation both before and after controlling for rs7208505 variation while genotype alone was not associated (FIG. 2A, Table 4).

Figure 2:
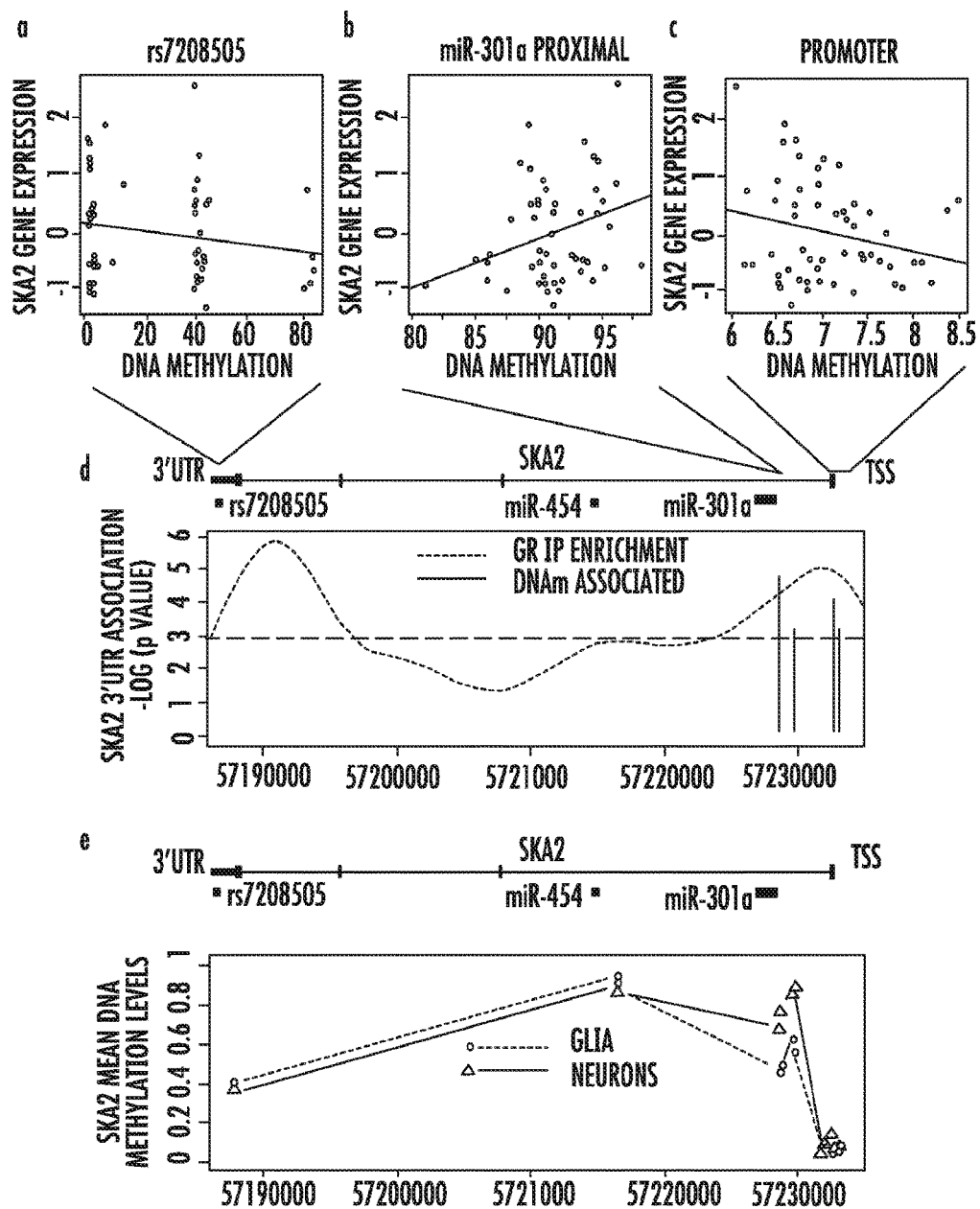
FIG. 2. Genomic regions regulating SKA2 gene expression. A. Scatterplot of the neuronal proportion adjusted SKA2 gene expression levels (y axis) as a function of DNA methylation at rs7208505 (x axis). B. Scatterplot of the neuronal proportion adjusted SKA2 gene expression levels (y axis) as a function of DNA methylation at miR-301a proximal CpG, cg19273756 (x axis). C. Scatterplot of the neuronal proportion adjusted SKA2 gene expression levels (y axis) as a function of DNA methylation at the SKA2 promoter, comprised of the mean methylation level of all exon1 and 5'UTR CpGs (x axis). D. Plot of the negative natural log of the significance of the association of rs7208505 genotype corrected SKA2 3'UTR DNA methylation vs. HM450 microarray CpGs located in the SKA2 gene (y axis) plotted as a function of genomic coordinate (x axis). For methylation correlations, only N=32 C/T and C/C genotype individuals capable of DNA methylation modification were assessed in the correlation. SKA2 3'UTR DNA methylation associated CpGs were located primarily in two regions including proximal to miR-301a and within the gene promoter. CpGs included cg10822495 (rho=0.46, p=0.0083) and cg19273756 (rho=−0.38, p=0.035) proximal to miR-301a, and cg17663700 (rho=0.32, p=0.077), cg17989037 (rho=0.36, p=0.043), cg27512082 (rho=0.42, p=0.016), and cg24616461 (rho=0.32, p=0.074) located within the promoter region. Only those CpGs with associations below a trend level of p≤0.1 are depicted. Also depicted are regions of dose dependent GR immunoprecipitation (IP) based binding in response to dexamethasone derived using ENCODE data. E. Plot of mean DNA methylation level at those HM450 microarray CpGs located across SKA2 for N=58 NICHD samples. A schematic representation of the SKA2 gene is depicted at the top of panels d, and e to scale relative to the plotted data points complete with the location of intronic microRNAs and rs7208505.

To understand the effects of 3′UTR epigenetic variation on expression, we correlated rs7208505 variation to all other CpGs located across SKA2 using available microarray data. Significant correlations were observed in neuronal but not glial DNA in two regions including promoter CpGs flanking a CREB binding site and upstream of an intronic microRNA, miR-301a (FIG. 2). Epigenetic variation in these regions showed opposing effects on SKA2 gene expression (FIG. 2). Average levels of DNA methylation of CpGs in the region upstream of miR-301a were lower in glial relative to neuronal DNA, possibly accounting for the neuron specific associations observed in this region (FIG. 2F). Together, rs7208505 epigenetic and genetic variation interacted with promoter and miR-301a proximal epigenetic variation to explain 39.52% of SKA2 gene expression as compared to the 16% explained by the model with rs7208505 variation alone (Table 4).

TABLE 3

| Gene expression associations | | | |
|---|---|---|---|
| Model Term | Spearman's ρ | DF | P value |
| Uncorrected 3′UTR DNAm | | | |
| 3′UTR DNAm | −0.31 | 52 | 0.022 |
| Model Term | Kruskal-Wallis $\chi^2$ | DF | P value |
| Uncorrected rs7208505 | | | |
| rs7208505 | 1.55 | 2 | 0.46 |
| Model Term | β value | Error | P value |
| rs7208505 Genetic and Epigenetic Model | | | |
| 3′UTR DNAm | −0.032 | 0.014 | 0.024 |
| rs7208505 C/T | 1.1 | 0.56 | 0.054 |
| rs7208505 C/C | 2.1 | 1.2 | 0.085 |
| F | 1 | | |
| DF | 44 | | |
| Model R2 | 0.16 | | 0.43 |
| Interactive Model | | | |
| 3′UTR DNAm | −8.5 | 2.9 | 0.0054 |
| Promoter | −2266 | 1470 | 0.13 |
| miR-301a | −168 | 115 | 0.15 |
| rs7208505 C/T | 1 | 0.52 | 0.063 |
| rs7208505 C/C | 1.2 | 1.1 | 0.29 |

TABLE 3-continued

| Gene expression associations | | | |
|---|---|---|---|
| Neuronal Proportion | 0.015 | 0.012 | 0.19 |
| 3′UTR DNAm X Promoter | 119 | 41 | 0.0062 |
| 3′UTR DNAm X miR-301a | 9.5 | 3.2 | 0.0054 |
| Promoter X miR-301a | 2508 | 1645 | 0.13 |
| 3′UTR DNAm X Promoter X miR-301a | −1.34 | 4.63 | 0.0061 |
| F | 2.8 | | |
| DF | 43 | | |
| Model R2 | 0.4 | | 0.009 |

DNAm = DNA methylation

We investigated relationships within the other CpGs located within SKA2 that were present on the microarray in order to understand the potential mechanisms by which 3′UTR epigenetic variation may influence gene expression.

One CpG (Illumina Probe: cg10822495) located within miR-301a within intron 1 of SKA2 was significantly associated with neuronal but not glial genotype corrected 3′UTR DNA methylation; however this CpG was not associated with SKA2 gene expression. Average levels of DNA methylation of CpGs in the region upstream of the miR-301a were lower in glial relative to neuronal DNA (FIG. 2E), possibly accounting for the observed neuron specific correlations of DNA methylation with gene expression.

We reasoned that rs7208505 T/T homozygotes that cannot be methylated may be reducing the sensitivity of the correlation across other SKA2 CpGs. Removal of these individuals resulted in numerous significant correlations of SKA2 3′UTR DNA methylation at rs7208505 with other CpGs. Using publically available ENCODE data, we determined the regions of dose responsive GR binding in response to dexamethasone and determined that many of the observed correlations are localized in GR binding regions across SKA2 (FIG. 2D). Two of these CpGs, cg17989037, and cg27512082, immediately flank the CREB binding site shown to be important for SKA2 gene expression[8]. Out of the above implicated CpGs correlating with rs7208505 epigenetic variation, only the miR proximal CpG, cg19273756, demonstrated evidence for moderate association to SKA2 gene expression levels after correcting for neuronal proportion as quantified by fluorescence activated cell sorting (F=4.13, df=51, p=0.022) (FIG. 2B). We averaged all CpG methylation inclusive and upstream of the first exon of SKA2 to obtain an average promoter region methylation signature, which exhibited a trend towards decreasing SKA2 gene expression (F=2.88, df=51, p=0.065) (FIG. 2C). We modeled epigenetic variation in the promoter, miR proximal region, and 3′UTR and identified a significant three way interaction that accounted for 39.52% of the variance in SKA2 gene expression (F=2.8, df=10/43, p=0.009). Cumulatively, the data suggest that epigenetic variation in the SKA2 3′UTR may be a reflection of GR dependent epigenetic reprogramming However, variation in gene expression was not accounted for by variation in any one region implicated in GR binding, suggesting other factors beyond GR mediated epigenetic change may be important for altering expression. As noted in previous analyses, rs7208505 genetic variation was not independently associated with SKA2 gene expression measures, while DNA methylation variation at rs7208505 was (Table 4). As the genetic and epigenetic variation at rs7208505 are highly correlated, it is difficult to ascertain the effects of genotype statistically independently from DNA methylation at rs7208505. In the case of DNA methylation, there is an additional level of variation beyond the genotype alone that allows it to be more informative after correction for genotype. Despite this, there remains the possibility that rs7208505 may exert effects on gene expression through alternative mechanisms. As an exploratory analysis, we investigated for the presence of long range genetic variation occurring in linkage disequilibrium (LD) with rs7208505. First, we tested each CpG on the microarray for association to rs7208505 genetic variation alone. DNA methylation at the miR-301a proximal CpG, cg19273756, exhibited a trend towards association with rs7208505 (F=1.8, df=55, p=0.063), we investigated genetic variants within 2 kb of the miR-301a. Two genetic variants were located in this region, including rs7502947 and rs58604484. These variants encode a C/T transition and an insertion of the sequence : AACTAGCATTGACTATT (SEQ ID NO:11) on the antisense strand, both of which exhibit similar minor allele frequencies around 50% as the alternative C allele of rs7208505 according to the dbSNP database (http://www.ncbi.nlm.nih.gov/SNP). Genomic sequences containing alternate alleles of these variants were input into the MATCH algorithm (http://www.gene-regulation.com/cgi-bin/pub/programs/match/bin/match.cgi) to search the TRANSFAC database for differential transcription factor binding motifs created by these sequence variants. Using a stringent matrix similarity cut off of 0.9 and core similarity cut off of 0.75, the insertion at rs58604484 generated a binding site for a single transcription factor, AP-1.

Figure 3:
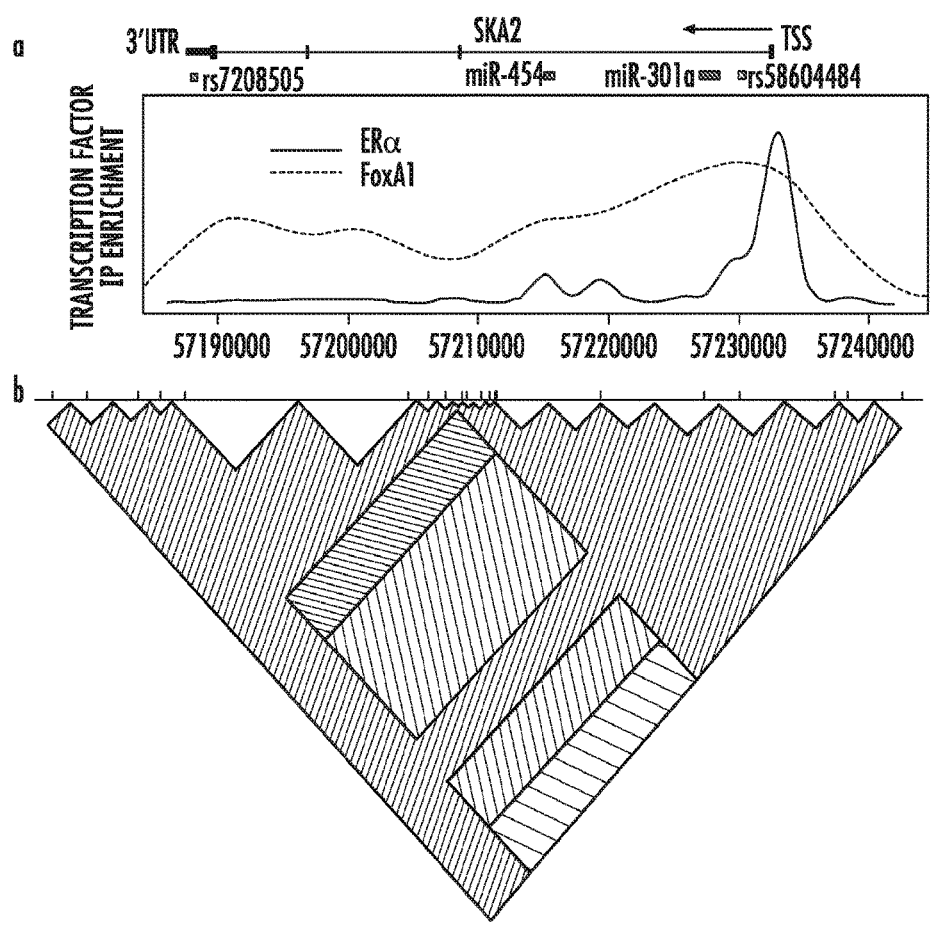
FIG. 3. Transcription factor binding and linkage disequilibrium across SKA2. A. Density plots of regions binding ERα and FOXA1 transcription factors from ENCODE data in the region of SKA2. B. An LD plot generated using HapMap (http://hapmap.ncbi.nlm.nih.gov/cgi-perl/gbrowse/hapmap27_B36) demonstrating the strength of LD with stronger dprime values depicted in increasing shades of red. A schematic of SKA2 is depicted to scale to denote the positions of rs7208505 and rs58604484 as a function of both LD and transcription factor binding.

Interestingly, recent research has demonstrated that GR binding may occur at estrogen receptor alpha (ERα) binding elements (EREs) after stimulation with dexamethasone, but that this binding requires the facilitation of both FOXA1 and AP-1.[9] ENCODE annotation tracks implicate a FOXA1 binding site is located approximately 200 by downstream of rs58604484, while MATCH identifies an ERE approximately 30 by downstream of rs58604484. Investigation of FOXA1 and ERα immunoprecipitation peaks from ENCODE data confirm the presence of these transcription factors at the predicted locations upstream of the miR-301a (FIG. 3). Taken together, the results suggest that creation of an AP-1 binding site through an insertion mutation at rs58604484 in linkage disequilibrium with rs7208505 may facilitate the occupation of an ERE by GR and lead to alteration of miR-301a proximal DNA methylation at cg19273756. This potential mechanism by which rs7208505 genetic variation may influence expression should be validated with future experimental studies.

Replication in peripheral tissues. We assessed the association of SKA2 variation with suicidal ideation in peripheral blood samples from the three living cohorts. Across all samples, significant rs7208505 DNA methylation elevations were observed consistent with the brain findings (FIG. 1D, 1E, Table 3). Model factors were significant among the 30 women in the prospective cohort who provided blood samples months prior to the suicidal ideation measurement (Table 5). The consistent associations of the model from these earlier time points suggested that DNA methylation variation at SKA2 preceded the transition to forming suicidal thoughts; however, this interpretation would not be correct if the levels of suicidal ideation were comparable between the earlier time points and the third trimester period at which suicidal ideation was measured. To evaluate this possibility, the change in suicidal ideation was investigated from third trimester relative to the earlier time points. Both increases and decreases in suicidal ideation were observed from the earlier trimesters to the third trimester Importantly, the change in suicidal ideation from first and second trimester to third trimester was also associated (Table 5), suggesting that SKA2 3'UTR DNA methylation variation associated with suicidal ideation precedes the transition to the ideating state. Weighted gene co-expression network analysis (WGCNA)[10] in brain and blood derived data provided supporting evidence that peripheral epigenetic variation is a marker of primarily neuronal processes.

TABLE 5

Prospective Suicidal Ideation Associations

| Model Terms | 3rd Trimester Suicidal Ideation from 1st and 2nd Trimester Blood (N = 30) | | | 2nd-3rd Trimester Suicidal Ideation (N = 30) | | |
|---|---|---|---|---|---|---|
| | β value | Error | P value | β value | Error | P value |
| DNAm | 0.056 | 0.013 | $1.5 \times 10^{-4}$ | 0.061 | 0.026 | 0.025 |
| C/T | −2.5 | 0.66 | $7.2 \times 10^{-4}$ | −2.8 | 1.4 | 0.046 |
| C/C | −5.1 | 1.2 | $2.1 \times 10^{-4}$ | −5 | 2.4 | 0.048 |
| Age | 0.036 | 0.015 | 0.029 | 0.023 | 0.032 | 0.48 |
| F | 6.2 | | | 1.6 | | |
| DF | 25 | | | 25 | | |
| Model $R^2$ | 0.5 | | 0.0013 | 0.2 | | 0.22 |

DNAm = DNA methylation

C/T = rs7208505 heterozygotes

C/C = rs7208505 alternative homozygotes

* While psychiatric medication changes may have occurred over this period in women becoming depressed during the third trimester, controlling for third trimester antenatal depression status as an additive covariate did not alter the significance of any model factors reported above. Similarly, controlling for blood cellular heterogeneity using cell subtype proportions reported previously[11] did not affect the significance of the model.

Figure 4:
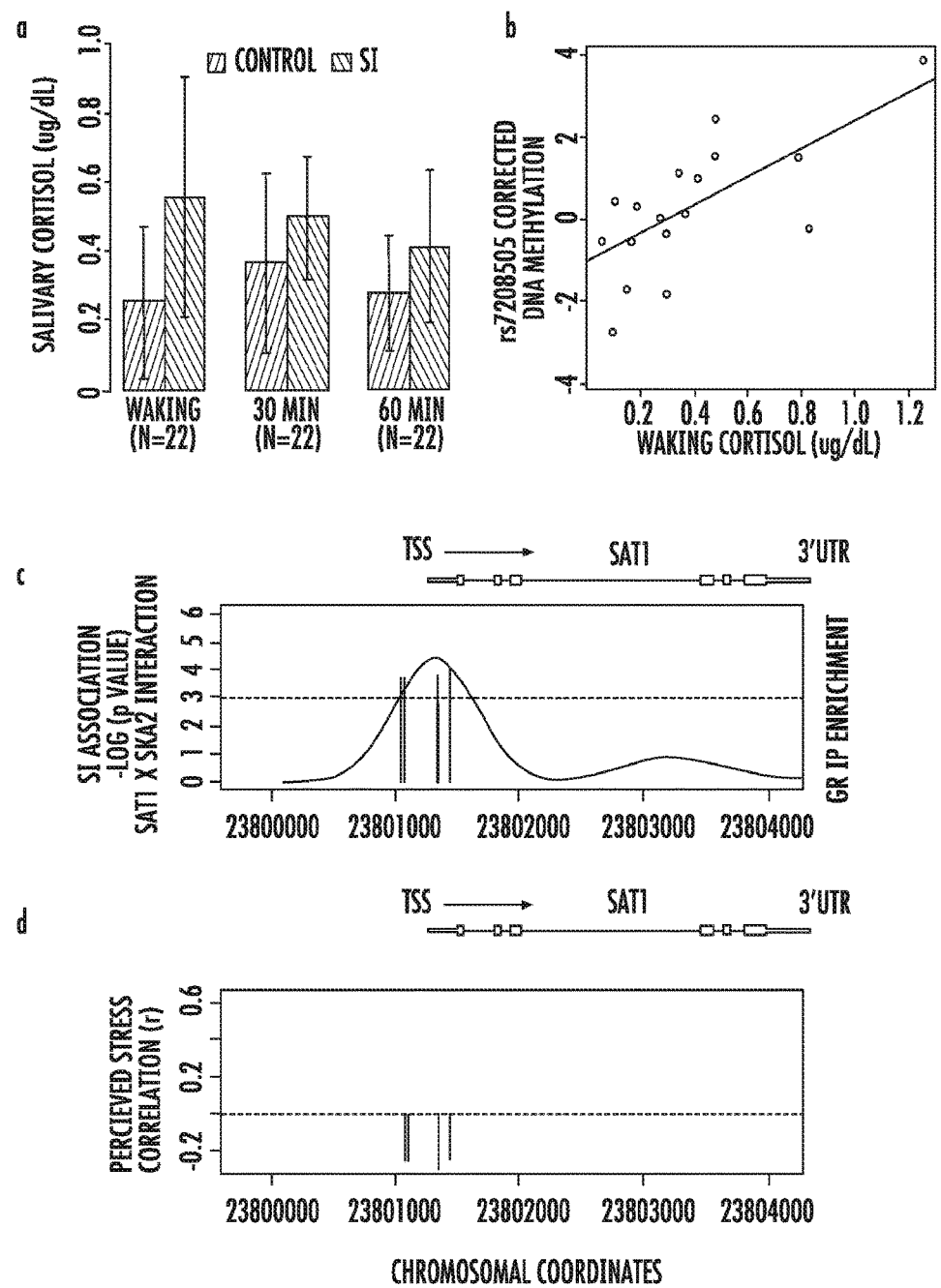
FIG. 4. Glucocorticoid relationships to suicidal ideation and suicidal ideation related genes. A. Barplot of salivary cortisol levels between suicidal ideation and controls in the GenRED cohort at waking (Wilcoxon Rank Sum, W=13.5, df=8.8, p=0.018) , 30 min (Wilcoxon Rank Sum, W=23, df=16.09, p=0.12), and 60 min (Wilcoxon Rank Sum, W=27, df=10, p=0.22) after waking. Error bars represent standard deviations. B. Scatterplot of rs7208505 corrected DNA methylation (y axis) as a function of waking cortisol levels (x axis) in the GenRED offspring cohort (F=14.69, df=17, p=0.0013). C. A plot of the—natural log of the significance of CpGs within the SAT1 gene with suicidal ideation as measured by MADRS in the prospective cohort (y axis) as a function of genomic coordinate (x axis). Associations of SAT1 appear in blue and associations of interaction with SKA2 3'UTR DNA methylation appear in red. Only CpGs reaching statistical significance or trend level are depicted. A CpG at Illumina probe cg18154784 interacted with rs7208505 genetic and epigenetic variation to significantly associate with suicidal ideation (F=4.47, df=43, p=8.2×10$^{-4}$). The frequency of ENCODE GR immunoprecipitation peaks are depicted in black.

Association of SKA2 with salivary cortisol. Using prospectively collected cortisol measurements in the GenRED offspring cohort, we assessed the ability of SKA2 3'UTR epigenetic and genetic variation to mediate suppression of cortisol levels. Waking cortisol was significantly associated with suicidal ideation in this cohort; however, cortisol taken at 30 min and 60 min was not associated nor were CpGs in the region directly upstream of rs7208505 (FIG. 4A). Only waking cortisol was significantly associated with epigenetic variation at rs7208505 (Table 6, FIG. 4B); however, as SKA2 is implicated in glucocorticoid signaling, we reasoned that cortisol levels may interact with SKA2 to mediate suppression of future cortisol. Prospective investigation of the interaction of waking cortisol with SKA2 3'UTR epigenetic and genetic variation was significantly associated with the reduced suppression of cortisol from the 30 to 60 minute time points (Table 6). SKA2 mediated changes in glucocorticoid signaling may influence and interact with other suicidal ideation related biological variation, such as promoter CpGs in the SAT1 gene (FIG. 4C, D) where gene expression has been previously implicated in suicidal behavior[12]. As an exploratory analysis, we assessed CpGs located within suicidal ideation and suicide attempt associated SAT1[12] and identified a trend for an interaction with SKA2 3'UTR epigenetic and genetic variation with a promoter CpG located within an ENCODE implicated GR binding region (FIG. 4C, D), suggesting that SKA2 mediated changes in glucocorticoid signaling may influence and interact with other suicidal ideation related biological variation.

TABLE 6

Interactive effects on suicide risk

| Model Terms | PRC suicide attempt (N = 79) β value | Error | P value | PRC suicide attempt (N = 48) β value | Error | P value |
|---|---|---|---|---|---|---|
| DNAm | −0.0034 | 0.003 | 0.26 | −0.0026 | 0.0057 | 0.64 |
| C/T | −0.0064 | 0.16 | 0.97 | −0.51 | 0.31 | 0.11 |
| C/C | 0.34 | 0.26 | 0.19 | 0.20 | 0.46 | 0.67 |
| Anx | −0.54 | 0.29 | 0.064 | −0.94 | 0.89 | 0.30 |
| Age | −0.0094 | 0.024 | 0.7 | −0.032 | 0.047 | 0.51 |
| Sex | 0.07 | 0.12 | 0.55 | 0.11 | 0.22 | 0.64 |
| DNAm X Anx | 0.017 | 0.0084 | 0.053 | 0.026 | 0.015 | 0.08 |
| C/T X Anx | −0.23 | 0.50 | 0.63 | 0.098 | 0.83 | 0.90 |
| C/C X Anx | −1.56 | 0.87 | 0.078 | na | na | na |
| F | 0.97 | | | 2 | | |
| DF | 65 | | | 37 | | |
| Model $R^2$ | 0.16 | | 0.49 | 0.353 | | 0.061 |

| Model Terms | GenRED Waking Cortisol (N = 22) β value | Error | P value | GenRED Cortisol Suppression (N = 22) β value | Error | P value |
|---|---|---|---|---|---|---|
| DNAm | 0.12 | 0.035 | 0.0037 | −0.01 | 0.012 | 0.41 |
| C/T | −4.7 | 1.5 | 0.0068 | 0.2 | 0.48 | 0.69 |
| C/C | −11 | 3.2 | 0.004 | 1.1 | 1.1 | 0.34 |
| Age | −0.0094 | 0.019 | 0.62 | −0.017 | 0.004 | 0.00 |
| Sex | 0.037 | 0.1 | 0.72 | −0.06 | 0.023 | 0.03 |
| Cort | | | | −0.094 | 0.54 | 0.86 |
| DNAm X Cort | | | | −0.11 | 0.02 | 0.00 |
| C/T X Cort | | | | 5.6 | 1 | $4.1 \times 10^{-4}$ |
| C/C X Cort | | | | 10 | 1.9 | $5.5 \times 10^{-5}$ |
| F | 5.2 | | | 27 | | |
| DF | 13 | | | 9 | | |
| Model $R^2$ | 0.67 | | 0.0075 | 0.96 | | $1.8 \times 10^{-5}$ |

DNAm = DNA methylation
C/T = rs7208505 heterozygotes
C/C = rs7208505 alternative homozygotes
Anx = anxiety
Cort = waking cortisol
X denotes an interaction We assessed the effect of early life trauma on suicidal phenotype in the model with SKA2 genetic and epigenetic variation. In the GenRED offspring cohort, all model terms were significant including rs7208585 genotype (C/T β=0.65±0.27, p=0.031; C/C β=1.08±0.41, p=0.019), SKA2 3'UTR DNA methylation (β=−0.011±0.0044, p=0.025), and trauma (β=0.86±0.21, p=0.0015) in an additive model ($R^2$=0.62 p=0.0051). In the prospective cohort, early childhood abuse was not significantly associated with suicidal ideation in an additive model. We investigated a third peripheral blood cohort of N=48 SA cases and N=278 non-SA controls called the PRC cohort. In this sample, early childhood sexual abuse was significantly associated with SA cases (β=3.26±0.081, p=6.9×10$^{-5}$); however, SKA2 3'UTR DNA methylation and rs7208505 genotype were not associated. Detailed information on drug and alcohol use measures enabled a subsequent analysis of factors potentially skewing SKA2 3'UTR DNA methylation. No variables survived Bonferroni correction (N=26 tests); however, only "alcohol abuse" displayed a nominally significant association with rs7208505 corrected DNA methylation (β=−1.64±0.79, p=0.038). As alcohol intake can raise glucocorticoid levels[33] a possibility is that alcohol abuse occurring in a subset of individuals is altering SKA2 3'UTR DNA methylation indirectly through the glucocorticoid pathway. We found that SKA2 3'UTR DNA methylation was significantly associated with suicide attempt and interacted with alcohol abuse (Table 3). Incorporation of early life trauma as an additive covariate increased the model $R^2$ from 0.077 to 0.17 (p=4.5×10$^{-8}$) and resulted in the rs7208505 C/C genotype to exhibit a trend towards association (C/C β=0.17±0.1, p=0.098).

Interaction of SKA2 with anxiety and stress. We observed a significant interaction of both perceived stress scores and anxiety scores with rs7208505 genotype and DNA methylation in predicting suicidal ideation in the prospective cohort (Table 7, FIG. 5). This association was replicated in the GenRED offspring cohort, where anxiety interacted with rs7208505 epigenetic and genetic status to moderate suicide attempt, but not suicidal ideation (Table 7). In the PRC cohort, the anxiety interaction model was associated with suicidal ideation; however, the association became even stronger in the subset with suicide attempt (Table 7, FIG. 5). The SKA2 3'UTR DNA methylation interaction with anxiety was significantly associated suicide attempt in those with suicidal ideation (Table 6). Finally, a DNA methylation anxiety interaction non-significant trend was observed in distinguishing those with suicide attempt and intent to die from those with suicide attempt without intent to die (Table 6). Cumulatively, our data suggest that epigenetic variation at SKA2 could increase risk for suicidal ideation and, among ideators with anxiety or stress, suicide attempt is more likely.

TABLE 7

Interactive effects on suicidal behavior

| Model Terms | Sample | | | | | |
|---|---|---|---|---|---|---|
| | Prospective Suicidal Ideation (N = 31) | | | GenRED Offspring Suicide Attempt (N = 22) | | |
| | β value | Error | P value | β value | Error | P value |
| DNAm | −0.074 | 0.048 | 0.14 | 0.0054 | 0.039 | 0.89 |
| C/T | 2.66 | 2.32 | 0.27 | −0.23 | 1.6 | 0.89 |
| C/C | 6.30 | 4.42 | 0.17 | −0.34 | 3.5 | 0.92 |
| Anxiety | −0.13 | 0.13 | 0.31 | −0.32 | 0.3 | 0.3 |
| Age | 0.010 | 0.014 | 0.48 | 0.039 | 0.025 | 0.15 |
| Sex | na | na | na | 0.21 | 0.13 | 0.14 |
| DNAm X Anxiety | 0.049 | 0.016 | 0.007 | 0.21 | 0.08 | 0.02 |
| C/T X Anxiety | −1.92 | 0.78 | 0.025 | −7.8 | 3.2 | 0.031 |
| C/C X Anxiety | −4.18 | 1.46 | 0.011 | −18 | 7.1 | 0.024 |
| F | 6.8 | | | 4.3 | | |
| DF | 17 | | | 11 | | |
| Model $R^2$ | 0.8 | | 0.00032 | 0.8 | | 0.012 |

| Model Terms | Sample | | | | | |
|---|---|---|---|---|---|---|
| | PRC Suicidal Ideation (N = 325) | | | PRC Suicide Attempt (N = 325) | | |
| | β value | Error | P value | β value | Error | P value |
| DNAm | 0.001 | 0.0012 | 0.37 | $3.7 \times 10^{-4}$ | $9.7 \times 10^{-4}$ | 0.70 |
| C/T | −0.017 | 0.064 | 0.79 | −0.014 | 0.053 | 0.79 |
| C/C | −0.047 | 0.11 | 0.66 | 0.054 | 0.088 | 0.54 |
| Anxiety | 0.15 | 0.15 | 0.32 | −0.11 | 0.12 | 0.36 |
| Age | 0.004 | 0.01 | 0.66 | 0.0017 | 0.008 | 0.83 |
| Sex | −0.03 | 0.05 | 0.58 | −0.01 | 0.040 | 0.87 |
| DNAm X Anxiety | 0.009 | 0.004 | 0.033 | 0.0106 | 0.0036 | 0.0039 |
| C/T X Anxiety | −0.39 | 0.24 | 0.10 | −0.11 | 0.20 | 0.57 |
| C/C X Anxiety | −0.98 | 0.41 | 0.02 | −0.95 | 0.34 | 0.006 |
| F | 2.6 | | | 1.9 | | |
| DF | 312 | | | 312 | | |
| Model $R^2$ | 0.09 | 0.003 | 0.003 | 0.067 | | 0.037 |

Race was adjusted for in all models but data are not shown due to space.
DNAm = DNA methylation
C/T = rs7208505 heterozygotes
C/C = rs7208505 alternative homozygotes
X denotes an interaction Prediction of suicidal behavior. We assessed the ability of our statistical model to predict suicidal ideation in peripheral tissues of living samples. We used suicide attempt data from the PRC cohort to generate an additive linear model of rs7208505 genotype and SKA2 3'UTR DNA methylation interacting with anxiety status, controlling for age and sex as covariates. Using anxiety status as the interactive covariate, the GenRED cohort predicted suicidal ideation with an area under the of the receiver operator characteristic curve of 0.71 (95% CI=0.42:1); however, use of salivary cortisol levels as the interactive covariate improved the area under the curve to 0.82 (95% CI=0.60:1) (FIG. 6A). The model generated an AUC of 0.55 in the PRC sample. As mentioned above, a possibility is that alcohol abuse occurring in a subset of individuals is interfering with accurate retrospective prediction and as such, those individuals with a history of alcohol abuse and alcohol dependence were excluded from the model. The linear model predicted the remaining N=27 SA cases and N=221 controls with an AUC of 0.66. Using a bootstrapping technique and a history of alcohol abuse or dependence in the model as an interactive covariate and early life trauma as an additive covariate, we predicted SA status on the entire PRC sample (N=40 suicide attempt, N=232 non-suicide attempt due to missing information on early life trauma) with an AUC of 0.71. Inclusion of ethnicity into the model increased the AUC to 0.72. We hypothesized that the long duration between suicide attempt in many samples may lead to a drift of epigenetic regulation, possibly in response to substance abuse variables in this population. To test this, we limited the sample to N=3 suicide attempt cases with an attempt within 2 years of blood draw and 192 cases with no history of SA and generated an AUC of 0.86. As highly lethal attempts resemble suicide clinically, biologically and possibly epigenetically, we reclassified all samples answering 'NO' to an intention to die as non-attempters, resulting in N=30 suicide attempt cases and N=296 non-suicide attempt cases and generated an AUC of 0.76. In the prospective sample, the perceived stress metric at the time of blood draw was used as the interactive covariate, resulting in suicidal ideation prediction AUC of 0.80 (95% CI=0.64:0.97) (FIG. 6A). Limiting the sample to prospective prediction of those 30 women where 3$^{rd}$ trimester suicidal ideation was predicted from 1$^{st}$ or 2$^{nd}$ trimester blood generated an AUC of 0.79 (95% CI=0.42:1) (FIG. 6B). Increasing the stringency of the threshold to define suicidal ideation (see Supplementary Methods) resulted in improved model performance across both comparisons in this cohort (All women, N=51, AUC=0.91, 95% CI=0.8:1; $1^{st}$ or $2^{nd}$ trimester women, N=30, AUC =0.96, 95% CI=0.89: 1). In the GenRED cohort, the model predicted those N=4 suicide attempters from the sample with an AUC of 0.97 (95% CI=0.89:1) (FIG. 6B).

Functional classification of SKA2. We performed weighted gene co-expression network analysis (WGCNA)[34], followed by gene ontology analysis of significant co-regulated networks for the neuronal and glial cortical samples to assess the cell type specific function of genotype corrected SKA2 DNA methylation. WGCNA in blood derived data from the prospective cohort was assessed to generate an indication of whether peripheral epigenetic variation is a marker of neuronal or glial processes. We limited networks to those demonstrating significant non-parametric correlation between module membership and correlation significance per group. Genes within identified SKA2 co-regulated modules were assessed for over-represented gene pathways using the g.Profiler analysis suite[35]. Significant modules were detected in neurons (Rho=0.41, p=0.026) and blood (Rho=0.4, p=0.003), where an enrichment for genes within the category 'Axon Guidance' was observed in both neurons (KEGG04360: Observed=0.075, Expected=0.023, p=0.04) and blood (KEGG04360: Observed=0.12, Expected=0.016, p=0.019). Other neuron specific processes were enriched in the blood derived co-regulated module including 'Transmission of Nerve Impulse' (GO:0035637: Observed=0.087, Expected=0.064, p=0.023) and 'Synaptic Transmission' (GO:0035637: Observed=0.088, Expected=0.056, p=0.03), suggesting that epigenetic variation in brain relevant processes are being detected in peripheral blood.

In glia, a single module of SKA2 3'UTR co-regulated genes was identified that demonstrated significant over representation of a Biogrid interaction pathway containing the PARP1, MAD1L1, and SYN2 genes (Frequency observed=0.33, Frequency expected=0.023, p=0.022).

We attempted to ascertain the ability of DNA methylation levels to act as proxies of the perceived stress, anxiety, or cortisol measurements used in model prediction. To that end, we first built a predictive linear model of suicidal behavior varying as a function of DNA methylation at SKA2 and rs7208505 genotype interacting with stress, after controlling for age and sex as additive covariates. Using genome-wide DNA methylation data in three datasets, we attempted to predict suicidal behavior using each of the ~480,000 CpG dinucleotides measured on the Illumina Human Methylation 450 microarray in place of the interactive stress component. The performance of model prediction was measured using the AUC metric. Concurrently, we assessed for those loci correlating with salivary cortisol measures in the GenRED offspring cohort to identify those CpGs that appear to act as markers of HPA axis function. We identified a significant over-representation of CpGs where salivary cortisol significantly increases DNA methylation with those CpGs capable of predicting suicidal behaviors above the $99^{th}$ percentile of the AUCs obtained per cohort. This finding means that CpGs that act as markers of HPA axis function were among those CpGs that generated the highest suicidal behavior prediction accuracies (FIG. 7).

In our first strategy, we selected CpGs demonstrating a significant positive non-parametric Spearman correlation with salivary cortisol levels below a p value threshold of 0.001 as those loci best able to act as stress proxies in our suicidal behavior prediction model. These loci are depicted in Table 8. A significant over-representation of calcium signalling was observed among genes associated with these loci (GO:0005509: Freq Expected=0.017, Freq Observed=0.15, p=0.04), which has been shown to be disregulated in response to inflammation and stress[13-15].

Concurrently, in search of DNA methylation proxies capable of improving suicidal behavior prediction, we simply selected those loci with consistently the highest AUC across both the GenRED offspring cohort, the prospective cohort, and either the neuronal or glial cohort. Seven loci were identified according to this second strategy (Table 8).

TABLE 8

CpG loci used as stress proxy in prediction model

| Illumina Probe ID | Spearman's Rho | Correlation P value | NICHD Neuron (AUC) | GenRED Offspring (AUC) | Prospective Cohort (AUC) | Chr | Position (hg19) | Gene |
|---|---|---|---|---|---|---|---|---|
| Strategy 1: Loci with significant positive association to salivary cortisol | | | | | | | | |
| cg00039070 | 0.75 | 0.00051 | 0.52 | 0.89 | 0.76 | 7 | 1.3E+08 | EXOC4 |
| cg00087645 | 0.73 | 0.00078 | 0.52 | 0.89 | 0.76 | 6 | 1.6E+08 | |
| cg00213044 | 0.74 | 0.00063 | 0.47 | 0.91 | 0.75 | 12 | 5.3E+07 | KRT6A |
| cg00930306 | 0.80 | 0.00008 | 0.49 | 0.89 | 0.76 | 1 | 1.6E+08 | MUC1 |
| cg01042640 | 0.79 | 0.00012 | 0.48 | 0.88 | 0.71 | 16 | 7.4E+07 | CLEC18B |
| cg01055135 | 0.75 | 0.00051 | 0.49 | 0.89 | 0.70 | 1 | 1.7E+07 | MST1P2 |
| cg01190024 | 0.72 | 0.00100 | 0.56 | 0.95 | 0.74 | 10 | 8078357 | |
| cg01192531 | 0.77 | 0.00029 | 0.53 | 0.79 | 0.78 | 20 | 3.4E+07 | ROMO1 |
| cg01236166 | 0.74 | 0.00074 | 0.47 | 0.89 | 0.73 | 16 | 5.9E+07 | |
| cg01344859 | 0.74 | 0.00074 | 0.56 | 0.82 | 0.76 | 14 | 5.6E+07 | MAPK1IP1L |
| cg01764046 | 0.73 | 0.00095 | 0.49 | 0.89 | 0.74 | 1 | 3.2E+07 | HCRTR1 |
| cg02330818 | 0.73 | 0.00078 | 0.55 | 0.89 | 0.74 | 20 | 6.2E+07 | |
| cg03324654 | 0.73 | 0.00091 | 0.49 | 0.93 | 0.74 | 1 | 3.9E+07 | |
| cg03474461 | 0.83 | 0.00000 | 0.53 | 0.93 | 0.76 | 10 | 3.8E+07 | |
| cg03761216 | 0.87 | 0.00000 | 0.56 | 0.77 | 0.73 | 1 | 5.2E+07 | EPS15 |
| cg03842933 | 0.80 | 0.00009 | 0.49 | 0.91 | 0.74 | 4 | 1.6E+08 | DCHS2 |
| cg03952543 | 0.76 | 0.00043 | 0.48 | 0.91 | 0.71 | 6 | 1.2E+08 | FABP7 |
| cg04002486 | 0.73 | 0.00091 | 0.49 | 0.89 | 0.73 | 16 | 1162736 | |
| cg04117972 | 0.73 | 0.00082 | 0.50 | 0.89 | 0.75 | 1 | 2.3E+08 | |
| cg04194272 | 0.74 | 0.00063 | 0.49 | 0.93 | 0.72 | 20 | 3.4E+07 | |
| cg04203883 | 0.76 | 0.00036 | 0.48 | 0.88 | 0.75 | 12 | 5.4E+07 | HOXC11 |
| cg04508084 | 0.73 | 0.00078 | 0.49 | 0.93 | 0.74 | 5 | 1666974 | |
| cg04969220 | 0.76 | 0.00043 | 0.48 | 0.93 | 0.74 | 4 | 978723 | SLC26A1 |

TABLE 8-continued

CpG loci used as stress proxy in prediction model

| Illumina Probe ID | Spearman's Rho | Correlation P value | NICHD Neuron (AUC) | GenRED Offspring (AUC) | Prospective Cohort (AUC) | Chr | Position (hg19) | Gene |
|---|---|---|---|---|---|---|---|---|
| cg05141159 | 0.73 | 0.00082 | 0.56 | 0.91 | 0.73 | 16 | 1.1E+07 | DEXI |
| cg05329893 | 0.72 | 0.00100 | 0.53 | 0.88 | 0.73 | 4 | 7.1E+07 | AMTN |
| cg05403241 | 0.75 | 0.00057 | 0.50 | 0.57 | 0.71 | 2 | 1.2E+08 | |
| cg05692127 | 0.78 | 0.00020 | 0.54 | 0.95 | 0.73 | 2 | 5.6E+07 | PNPT1 |
| cg05865660 | 0.82 | 0.00002 | 0.50 | 0.45 | 0.74 | 4 | 1.9E+08 | |
| cg06058576 | 0.77 | 0.00026 | 0.50 | 0.93 | 0.76 | 5 | 506472 | SLC9A3 |
| cg06181567 | 0.77 | 0.00029 | 0.47 | 0.89 | 0.74 | 16 | 5.1E+07 | NOD2 |
| cg06382093 | 0.73 | 0.00095 | 0.55 | 0.89 | 0.73 | 18 | 7.7E+07 | |
| cg06698399 | 0.73 | 0.00086 | 0.53 | 0.89 | 0.72 | 20 | 6E+07 | CDH4 |
| cg07081770 | 0.73 | 0.00095 | 0.46 | 0.84 | 0.72 | 7 | 1.6E+08 | |
| cg07219955 | 0.76 | 0.00040 | 0.51 | 0.73 | 0.70 | 6 | 4.7E+07 | PLA2G7 |
| cg07961252 | 0.74 | 0.00060 | 0.52 | 0.96 | 0.73 | 17 | 5.9E+07 | BCAS3 |
| cg07972983 | 0.74 | 0.00067 | 0.55 | 0.82 | 0.76 | 1 | 2.1E+08 | RBBP5 |
| cg08202274 | 0.79 | 0.00016 | 0.54 | 0.93 | 0.77 | 3 | 1.8E+08 | |
| cg08224773 | 0.75 | 0.00054 | 0.53 | 0.89 | 0.74 | 8 | 1.1E+08 | FAM167A |
| cg08335245 | 0.79 | 0.00016 | 0.59 | 0.88 | 0.74 | 7 | 4.4E+07 | YKT6 |
| cg08395459 | 0.78 | 0.00020 | 0.50 | 0.71 | 0.70 | 4 | 4147958 | |
| cg08640046 | 0.72 | 0.00100 | 0.56 | 0.88 | 0.72 | 2 | 2.4E+08 | |
| cg08693671 | 0.77 | 0.00026 | 0.55 | 0.93 | 0.73 | 5 | 1.5E+08 | ANKH |
| cg08736034 | 0.73 | 0.00078 | 0.54 | 0.89 | 0.73 | 20 | 4.5E+07 | CDH22 |
| cg08764465 | 0.73 | 0.00082 | 0.48 | 0.89 | 0.70 | 8 | 1.5E+07 | |
| cg08776711 | 0.74 | 0.00074 | 0.53 | 0.89 | 0.75 | 7 | 1.4E+08 | DGKI |
| cg08829195 | 0.74 | 0.00063 | 0.48 | 0.91 | 0.71 | 16 | 1227293 | CACNA1H |
| cg08842584 | 0.77 | 0.00026 | 0.48 | 0.89 | 0.74 | 8 | 2E+07 | |
| cg09073106 | 0.78 | 0.00024 | 0.53 | 0.77 | 0.73 | 11 | 7.2E+07 | LRTOMT |
| cg09463917 | 0.73 | 0.00086 | 0.55 | 0.75 | 0.73 | 22 | 2.1E+07 | SCARF2 |
| cg09674093 | 0.79 | 0.00014 | 0.48 | 0.91 | 0.77 | 2 | 2.4E+08 | KLHL29 |
| cg09726509 | 0.75 | 0.00054 | 0.48 | 0.89 | 0.75 | 11 | 5.7E+07 | |
| cg10016024 | 0.78 | 0.00022 | 0.52 | 0.79 | 0.70 | 11 | 7.1E+07 | |
| cg10091299 | 0.80 | 0.00008 | 0.55 | 0.86 | 0.74 | 14 | 5.1E+07 | MAP4K5; ATL1; MAP4K5 |
| cg10477711 | 0.80 | 0.00011 | 0.48 | 0.91 | 0.76 | 2 | 1.2E+08 | |
| cg10568297 | 0.76 | 0.00043 | 0.55 | 0.66 | 0.71 | 7 | 5321676 | SLC29A4 |
| cg10970484 | 0.75 | 0.00057 | 0.50 | 0.79 | 0.71 | 14 | 1.1E+08 | C14orf180 |
| cg11564268 | 0.85 | 0.00000 | 0.53 | 0.82 | 0.75 | 16 | 7E+07 | NOB1 |
| cg11802469 | 0.76 | 0.00038 | 0.55 | 0.89 | 0.75 | 6 | 8.5E+07 | MRAP2 |
| cg12655059 | 0.74 | 0.00074 | 0.48 | 0.91 | 0.74 | 1 | 2.5E+08 | ZNF496 |
| cg13566150 | 0.73 | 0.00078 | 0.48 | 0.89 | 0.76 | 8 | 1.1E+08 | ANGPT1 |
| cg13712818 | 0.73 | 0.00086 | 0.46 | 0.93 | 0.72 | 17 | 5.4E+07 | |
| cg14051368 | 0.80 | 0.00009 | 0.54 | 0.91 | 0.71 | 11 | 1.7E+07 | ABCC8 |
| cg14183712 | 0.84 | 0.00000 | 0.52 | 0.73 | 0.72 | 7 | 1.6E+08 | PTPRN2 |
| cg14298689 | 0.77 | 0.00028 | 0.50 | 0.93 | 0.75 | 13 | 9.3E+07 | GPC5 |
| cg14520571 | 0.74 | 0.00074 | 0.53 | 0.91 | 0.74 | 1 | 1.5E+08 | RNF115 |
| cg14555811 | 0.77 | 0.00028 | 0.54 | 0.91 | 0.77 | 5 | 847052 | ZDHHC11 |
| cg14595922 | 0.73 | 0.00095 | 0.48 | 0.93 | 0.74 | 5 | 1.4E+08 | PCDHA6; PCDHA2; PCDHA1; PCDHA7; PCDHA1; PCDHA6; PCDHA5; PCDHA9; PCDHA9; PCDHA3; PCDHA4; PCDHA8 |
| cg14600384 | 0.76 | 0.00036 | 0.47 | 0.91 | 0.74 | 12 | 1.3E+08 | |
| cg15242223 | 0.76 | 0.00036 | 0.48 | 0.91 | 0.75 | 6 | 3E+07 | GABBR1 |
| cg15392911 | 0.76 | 0.00040 | 0.47 | 0.93 | 0.75 | 1 | 2.3E+08 | |
| cg16020210 | 0.75 | 0.00057 | 0.49 | 0.89 | 0.76 | 6 | 3489366 | |
| cg16118539 | 0.74 | 0.00063 | 0.48 | 0.91 | 0.75 | 10 | 2.3E+07 | |
| cg16339286 | 0.76 | 0.00033 | 0.52 | 0.91 | 0.72 | 7 | 4012484 | SDK1 |
| cg16380632 | 0.79 | 0.00017 | 0.48 | 0.93 | 0.74 | 1 | 7637516 | CAMTA1 |
| cg16415104 | 0.73 | 0.00095 | 0.49 | 0.66 | 0.76 | 4 | 3496300 | |
| cg16575461 | 0.73 | 0.00078 | 0.49 | 0.89 | 0.76 | 1 | 2225107 | SKI |
| cg16729016 | 0.73 | 0.00095 | 0.48 | 0.89 | 0.75 | 1 | 2.1E+08 | RPS6KC1 |
| cg16734981 | 0.76 | 0.00043 | 0.57 | 0.79 | 0.71 | 11 | 1.1E+08 | |
| cg17083475 | 0.83 | 0.00001 | 0.49 | 0.89 | 0.73 | 12 | 1.3E+08 | GALNT9 |
| cg17098147 | 0.82 | 0.00003 | 0.58 | 0.84 | 0.70 | 10 | 2.3E+07 | SPAG6 |
| cg17278793 | 0.73 | 0.00091 | 0.57 | 0.77 | 0.74 | 1 | 1.5E+08 | HIST2H2BF |
| cg17548347 | 0.76 | 0.00040 | 0.49 | 0.91 | 0.71 | 20 | 4.4E+07 | SPINT3 |
| cg18658663 | 0.78 | 0.00020 | 0.52 | 0.89 | 0.74 | 17 | 2595994 | KIAA0664 |
| cg18736791 | 0.82 | 0.00003 | 0.59 | 0.84 | 0.77 | 8 | 1.4E+08 | TSNARE1 |

TABLE 8-continued

CpG loci used as stress proxy in prediction model

| Illumina Probe ID | Spearman's Rho | Correlation P value | NICHD Neuron (AUC) | GenRED Offspring (AUC) | Prospective Cohort (AUC) | Chr | Position (hg19) | Gene |
|---|---|---|---|---|---|---|---|---|
| cg18770763 | 0.83 | 0.00000 | 0.48 | 0.89 | 0.73 | 11 | 724525 | EPS8L2 |
| cg18801459 | 0.75 | 0.00051 | 0.53 | 0.93 | 0.74 | 3 | 1.5E+08 | |
| cg18899999 | 0.75 | 0.00054 | 0.51 | 0.43 | 0.71 | 11 | 8.6E+07 | PICALM |
| cg19114050 | 0.73 | 0.00086 | 0.54 | 0.89 | 0.73 | 15 | 5.2E+07 | BCL2L10 |
| cg19233761 | 0.75 | 0.00045 | 0.48 | 0.89 | 0.71 | 3 | 1.8E+08 | HTR3C |
| cg19370054 | 0.73 | 0.00078 | 0.50 | 0.82 | 0.72 | 2 | 9.9E+07 | CNGA3 |
| cg19987705 | 0.77 | 0.00031 | 0.57 | 0.93 | 0.74 | 8 | 1.2E+08 | DERL1 |
| cg20368301 | 0.76 | 0.00033 | 0.48 | 0.77 | 0.71 | 12 | 1.1E+08 | |
| cg20546002 | 0.83 | 0.00002 | 0.52 | 0.91 | 0.70 | 5 | 1.8E+08 | COL23A1 |
| cg21048949 | 0.73 | 0.00086 | 0.56 | 0.86 | 0.78 | 11 | 1.2E+08 | BACE1 |
| cg21054080 | 0.78 | 0.00018 | 0.47 | 0.93 | 0.74 | 4 | 1.1E+08 | |
| cg21192370 | 0.73 | 0.00082 | 0.48 | 0.89 | 0.75 | 9 | 8.1E+07 | |
| cg21261709 | 0.75 | 0.00045 | 0.53 | 0.68 | 0.70 | 7 | 1E+08 | SRPK2 |
| cg21382232 | 0.75 | 0.00057 | 0.48 | 0.89 | 0.74 | 15 | 5.9E+07 | RNF111 |
| cg22177721 | 0.74 | 0.00063 | 0.55 | 0.89 | 0.72 | 6 | 1.4E+08 | |
| cg22908423 | 0.81 | 0.00006 | 0.49 | 0.88 | 0.71 | 14 | 1E+08 | |
| cg23031518 | 0.72 | 0.00100 | 0.50 | 0.93 | 0.72 | 14 | 8.9E+07 | SPATA7 |
| cg23481184 | 0.77 | 0.00028 | 0.47 | 0.93 | 0.78 | 15 | 3E+07 | FAM189A1 |
| cg24983752 | 0.76 | 0.00040 | 0.48 | 0.93 | 0.70 | 11 | 1.2E+08 | |
| cg26104239 | 0.77 | 0.00028 | 0.51 | 0.84 | 0.72 | 8 | 6.7E+07 | TRIM55 |
| cg26364080 | 0.78 | 0.00020 | 0.49 | 0.91 | 0.74 | 2 | 2.3E+08 | ARMC9 |
| cg26530557 | 0.76 | 0.00033 | 0.53 | 0.89 | 0.71 | 11 | 1.2E+08 | |
| cg26774205 | 0.73 | 0.00095 | 0.49 | 0.88 | 0.71 | 6 | 1.5E+08 | MTHFD1L |
| cg26945823 | 0.76 | 0.00038 | 0.49 | 0.89 | 0.74 | 16 | 6.5E+07 | |
| cg27199522 | 0.77 | 0.00031 | 0.48 | 0.91 | 0.76 | 16 | 8165100 | |
| cg27531982 | 0.73 | 0.00095 | 0.52 | 0.89 | 0.74 | 19 | 4.8E+07 | SLC8A2 |
| Strategy 2: Loci with consistently high AUC across cohorts | | | | | | | | |
| cg04481923 | 0.39 | 0.11 | 0.65 | 0.88 | 0.77 | 5 | 1.4E+08 | MIR886 |
| cg04717802 | −0.17 | 0.50 | 0.69 | 0.80 | 0.76 | 22 | 4.2E+07 | WBP2NL |
| cg07158503 | 0.17 | 0.50 | 0.65 | 0.86 | 0.78 | 5 | 1.4E+08 | |
| cg10942914 | 0.41 | 0.09 | 0.68 | 0.93 | 0.77 | 5 | 1.3E+08 | |
| cg13066461 | 0.23 | 0.36 | 0.69 | 0.86 | 0.77 | 11 | 1.9E+07 | MRGPRX2 |
| cg14708218 | 0.27 | 0.28 | 0.66 | 0.82 | 0.78 | 10 | 1.2E+08 | LOC399815; FAM24B |
| cg23624808 | 0.39 | 0.11 | 0.66 | 0.82 | 0.77 | 18 | 3.3E+07 | ZNF397OS |

Discussion

Using microarray technology to scan for epigenetic suicide associations, we identified a significant effect in a very small population of suicide decedents. The effect size of ~55% DNA methylation difference at SKA2 enabled this small sample size to have adequate power to survive correction for multiple testing, which was driven by the underlying genetic status of the rs7208505 SNP that abrogates the CpG dinucleotide. While microarray analysis was performed only in Caucasians, incorporation of both the genetic and epigenetic variation at this locus enabled replication across the entirety of the NICHD cohort, two additional post mortem brain cohorts, and three blood cohorts. Despite the striking consistency of the findings, the relatively small sample sizes of the studied cohorts suggest they represent promising but preliminary results warranting further study. The presented linear models implicated that DNA methylation and rs7208505 genotype may have opposing effects on suicidal behavior; however, as these metrics were highly correlated, the protective effects of rs7208505 may represent a statistical artifact. Analysis of genetic and epigenetic effects on suicidal behavior and gene expression separately indicated that DNA methylation alone may be the primary factor conferring risk. Importantly, the overall proportion of DNA methylation at rs720505 increases significantly with each successive C containing allele, suggesting that the underlying genetic architecture at rs7208505 may confer vulnerability by providing a genetic template for methylation changes to occur. This risk template would be expected to vary as a function of ethnicity, as allele frequencies for the C containing allele of rs7208505 are reportedly much lower in African Americans (~18%) compared to other ethnicities (~50-60%). Cumulatively, numerous consistent associations were observed with suicidal ideation, suicide attempt, and suicide completion, independent of variation in ethnicity and psychiatric diagnosis suggesting that variation in SKA2 may mediate risk for suicidal behaviors that progress from ideation, to attempt, to suicide.

SKA2 may influence suicidal phenotypes through its role in chaperoning the GR from the cytoplasm to the nucleus[7]. Rice et al. demonstrated that knockdown of SKA2 eliminated GR transactivation and response to dexamethasone treatment in vitro and that protein levels of SKA2 were decreased by glucocorticoid treatment, suggesting SKA2 gene expression may be a component of the glucocorticoid feedback inhibition system. In our data, SKA2 genetic and epigenetic differences were associated with reduced suppression of salivary cortisol after waking in the GenRED cohort. As blood was not drawn at the same time as salivary cortisol sampling, the causative role of DNA methylation must be interpreted cautiously. While DNA methylation variation at rs7208505 might be important for suicidal ideation etiology, it remains possible that this variation is a reflection of cortisol variation.

In the above model, SKA2 epigenetic and genetic variation represents an underlying state increasing suicide risk in the presence of a stressor. SKA2 epigenetic and genetic variation interacted with stress and anxiety metrics to mediate suicidal ideation in the prospective cohort, while in the PRC and GenRED offspring cohorts, the same model distinguished between individuals with suicidal ideation who transitioned to suicide attempt. It is important to note that the suicidal ideation, suicide attempt and suicide phenotypes are not interchangeable; however, in some individuals, they represent progressive stages of suicidal behavior that share many etiological factors. The proportion of variance accounted by our models was very high in some cohorts and leaves little room for the involvement of other factors. While our data suggest that SKA2 may be etiologically relevant to glucocorticoid signaling, it is possible that the detected epigenetic variation at SKA2 also represents a molecular record of suicide dysregulated glucocorticoid load over time and thus may be reflective of other sources of etiologically relevant variation at other suicide implicated loci. A recent report identified blood gene expression at SAT1 prospectively predicted both suicidal ideation and suicide attempt[12]. Our supplemental analysis demonstrated an interaction between SKA2 variation and DNA methylation at a CpG in the SAT1 promoter located within a region enriched for GR binding. SKA2 mediated failure to suppress normal stress response may play a role in SAT1 gene expression variation and could contribute to the transition from suicidal ideation to suicide attempt. Cumulatively, our data is consistent with an epidemiological study of 108,664 individuals in 21 countries that found disorders characterized by anxiety and poor impulse control predict the transition from suicidal ideation to suicide attempt[16].

One caveat with these analyses is that different metrics of suicidal ideation, suicide attempt, stress and anxiety were available across the studied cohorts. In the PRC and prospective samples, anxiety was reported by response to a single question, while the SCARED scale was used for the GenRED offspring. In the prospective cohort, we showed that anxiety, as measured by the Edinburgh Postnatal Depression Scale, was highly associated with perceived stress, which in another study was correlated with salivary cortisol levels[17]. Thus, it is possible the observed interactions of SKA2 with anxiety across cohorts are a reflection of underlying differences in stress and HPA axis response in anxious individuals. Despite these limitations, the ability of the PRC generated linear model to accurately predict both suicidal ideation and suicide attempt in the prospective and GenRED cohorts suggests that consistency was captured by these diverse metrics.

We performed WGCNA analysis in post mortem cortical neuron, glial, and blood cell derived microarray data and identified a relatively distinctive subset of genes co-regulated with SKA2 3'UTR DNA methylation. In both neurons and blood, SKA2 co-regulated networks were enriched for genes involved in axon guidance. Our data is consistent with reports demonstrating that early life trauma and associated elevated cortisol may inhibit prefrontal cortical synapse formation and attenuate regulation of the HPA axis[46] possibly through reduced inhibition of amygdala driven stress response.[36] In glia, enriched gene interactions identified numerous genes with potential functional relevance to psychiatric phenotypes. PARP1 has been directly associated with modulating astrocyte specific uptake of glutamate,[47] while epigenetic variation at SYN2 has been implicated in expression differences in bipolar disorder, major depression, and lithium treatment.[48,49] SYN2 functions at the tripartite synapse in astrocytes and plays a key role in modulating cross talk with neurons to promote neuronal synapse stabilization.[50,51] Together, the data suggest that factors involved in epigenetic reprogramming of the SKA2 3'UTR region may affect glial specific processes with relevance to neuronal synapse formation. One possibility is that exposure to stress may be causing epigenetic variation at both SKA2 and these co-regulated genes, a hypothesis which is consistent with the reports of glucocorticoid induced disruption of neuronal synapse stability.[52] Similar to previous studies identifying epigenetic biomarkers in a disease with a hormonal etiology,[53] the pathway analyses performed suggest that while not every gene may show evidence of cross tissue relevance to the brain, numerous genes in relevant pathways may record more of the etiologically relevant systemic epigenetic reprogramming events and thus be detectable in blood. The function of pathways specific genes appeared to be relevant to the known molecular processes of either neurons or glia in the analyses performed for each respective cell type. Importantly, our analyses demonstrate that epigenetic variation in blood co-regulated with brain specific epigenetic associations in suicide appear to mark brain specific biological processes.

Brain weight increases and cortical and adrenal hypertrophy have previously been associated with suicide,[2,54-56] and we observed a significant association of SKA2 genetic and epigenetic variation with brain weight in the SMRI cohort. Additionally, early life adversity has been associated with structural changes in numerous brain regions including various cortical regions, the anterior cingulate, corpus callosum, amygdala, and hippocampus.[2] These changes, in part, have been demonstrated to be the result of formation or regression of synaptic spines,[39,46] which is consistent with the enriched gene functions of SKA2 co-regulated gene networks. Yet another hypothesis warranting further testing is that suicide specific brain weight changes may be influenced by differences in glial proliferation throughout the brain, as SKA2 encodes a scaffold protein that is implicated in cell division.[57]

SKA2 gene expression decreases with suicide in NICHD brains associated primarily with isolated neuronal nuclei, suggesting the epigenetic dysregulation may be confined to neurons. The post mortem brain data was generated in the prefrontal cortex, a brain region with inhibitory connections to the HPA axis[18,19] and responsible for decision making, inhibition of negative thoughts, and impulsivity.[20,21] Reduction of GR transactivation is consistent with current models of suicide diathesis as GR gene expression reduction experiments in rodents mimic suicidal human characteristics,[22] exhibiting increases in corticosterone and helplessness in response to stress.[23]

The influence of SKA2 3'UTR epigenetic variation on gene expression appeared to be mediated by interaction with epigenetic variation within the gene promoter and proximal to intronic miR-301a, which has previously been shown to be reduced in post mortem prefrontal cortex of suicide completers.[24] Critically, miR-301a modulates SKA2 gene expression in A549 cell models by indirectly inhibiting CREB binding to the SKA2 promoter,[8] while the promoter CpGs shown to correlate with rs7208505 DNA methylation above directly flank this CREB binding site. As would be expected given the model, we observed a significant interaction of miR-301a and promoter CpG variation on SKA2 expression. The observed correlations of SKA2 3'UTR DNA methylation with other CpGs across the gene could result from common epigenetic reprogramming effects of GR binding, as the regions demonstrating correlations were located within GR immunoprecipitation peaks identified from ENCODE data. It is also possible that miR-301a proximal genetic variation in linkage disequilibrium with rs7208505 serve to alter GR recruitment, subsequently reprogramming DNA methylation in the region as discussed in the supplementary material. The miR-301a is an intronic microRNA and requires mRNA transcription of SKA2 to be generated by Drosha[25]. DNA methylation upstream of miR-301a may therefore result in co-transcriptional slowing and allow for spliceosomal interaction as occurs with inclusion of methylated alternative exons in alternatively spliced genes[26]. Elevated neuronal but not glial DNA methylation levels proximal to miR-301a suggests a possible functionally different effect of miR-301a in these two cell types. Importantly, while epigenetic variation proximal to the miR-301a and CREB binding site was associated with SKA2 gene expression, it was not associated with suicidal phenotypes.

While a growing number of studies are investigating epigenetic alterations in suicide,[1,27-32] few studies report biomarkers with high prediction accuracy. To our knowledge, the identified biomarker represents the first genetic and epigenetic biomarker capable of predicting suicidal ideation and suicide attempt in a prospective manner with over 80% accuracy from blood. The model performed remarkably well at predicting suicide attempt in the GenRED cohort; however, with 4 attempters, this result should be interpreted with caution. While the PRC cohort contained many more suicide attempt cases, we did not attempt prediction in this cohort as the time between suicide attempt and blood draw was greater than 10 years on average. Accumulating epigenetic change due to stochastic drift, substance use, and errors in retrospective reporting would call into question the reliability of the prediction. However, this highlights the fact that the cause vs. effect of prediction accuracy in the GenRED offspring sample must also be interpreted with care as the blood was taken after suicide attempt. Nevertheless, our data demonstrate very similar accuracies when predicting suicidal ideation in a prospective manner, suggesting SKA2 epigenetic and genetic variation may represent a trait influencing underlying suicide risk when interacting with stress. Cumulatively, the clinical implications of this finding are that early screening of those at risk for suicidal ideation and suicide attempt may be possible, allowing for the identification of individuals at risk, proactive treatment, and stress and anxiety reduction. The potential biomarker efficacy of our findings have relevance to numerous populations, for example, the military, where the identification of an underlying vulnerability may identify those individuals at risk for developing suicidal behaviors when exposed to the stress of war time situations. Future studies should be carried out to further evaluate the prospective efficacy of this finding in additional populations.

REFERENCES

1. Guintivano, J., Aryee, M. J., and Kaminsky, Z. A. (2013). A cell epigenotype specific model for the correction of brain cellular heterogeneity bias and its application to age, brain region and major depression. Epigenetics. 8(3), 290-302.

2. Birmaher, B., Brent, D. A., Chiappetta, L., Bridge, J., Monga, S., and Baugher, M. (1999). Psychometric properties of the Screen for Child Anxiety Related Emotional Disorders (SCARED): a replication study. J Am Acad Child Adolesc Psychiatry. 38(10), 1230-6.

3. Cox, J. L., Holden, J. M., and Sagovsky, R. (1987). Detection of postnatal depression. Development of the 10-item Edinburgh Postnatal Depression Scale. Br J Psychiatry. 150, 782-6.

4. Cohen, S., Kamarck, T., and Mermelstein, R. (1983). A global measure of perceived stress. J Health Soc Behav. 24(4), 385-96.

5. Kellam, S. G., Werthamer-Larsson, L., Dolan, L. J., Brown, C. H., Mayer, L. S., Rebok, G. W., Anthony, J. C., Laudolff, J., and Edelsohn, G. (1991). Developmental epidemiologically based preventive trials: baseline modeling of early target behaviors and depressive symptoms. Am J Community Psychol. 19(4), 563-84.

6. Kellam, S. G., Rebok, G. W., Ialongo, N., and Mayer, L. S. (1994). The course and malleability of aggressive behavior from early first grade into middle school: results of a developmental epidemiologically-based preventive trial. J Child Psychol Psychiatry. 35(2), 259-81.

7. Rice, L., et al. (2008). Identification and functional analysis of SKA2 interaction with the glucocorticoid receptor. J Endocrinol. 198(3), 499-509.

8. Cao, G., et al. (2010). Intronic miR-301 feedback regulates its host gene, ska2, in A549 cells by targeting MEOX2 to affect ERK/CREB pathways. Biochem Biophys Res Commun. 396(4), 978-82.

9. Karmakar, S., Jin, Y., and Nagaich, A. K. (2013). Interaction of glucocorticoid receptor (GR) with estrogen receptor (ER) alpha and activator protein 1 (AP 1) in dexamethasone-mediated interference of ERalpha activity. J Biol Chem. 288(33), 24020-34.

10. Langfelder, P. and Horvath, S. (2008). WGCNA: an R package for weighted correlation network analysis. BMC Bioinformatics. 9, 559.

11. Guintivano, J., Arad, M., Gould, T. D., Payne, J. L., and Kaminsky, Z. A. (2013). Antenatal prediction of postpartum depression with blood DNA methylation biomarkers. Mol Psychiatry.

12. Le-Niculescu, H., et al. (2013). Discovery and validation of blood biomarkers for suicidality. Mol Psychiatry.

13. Rayssiguier, Y., Libako, P., Nowacki, W., and Rock, E. (2010). Magnesium deficiency and metabolic syndrome: stress and inflammation may reflect calcium activation. Magnes Res. 23(2), 73-80.

14. Bali, A., Gupta, S., Singh, N., and Jaggi, A. S. (2013) Implicating the role of plasma membrane localized calcium channels and exchangers in stress-induced deleterious effects. Eur J Pharmacol. 714(1-3), 229-38.

15. Reznikov, O. H., Nosenko, N. D., and Sinitsyn, P. V. (2008). [Calcium-dependent mechanisms of stress disorders and noradrenergic responses of the hypothalamo-pituitary-adrenal system in neonatally androgenized female rats]. Fiziol Zh. 54(6), 24-9.

16. Nock, M. K., et al. (2009). Cross-national analysis of the associations among mental disorders and suicidal behavior: findings from the WHO World Mental Health Surveys. PLoS Med. 6(8), e1000123.

17. Bougea, A. M., Spandideas, N., Alexopoulos, E. C., Thomaides, T., Chrousos, G. P., and Darviri, C. (2013). Effect of the emotional freedom technique on perceived stress, quality of life, and cortisol salivary levels in tension-type headache sufferers: a randomized controlled trial. Explore (N.Y.). 9(2), 91-9.

18. Shonkoff, J. P. and Garner, A. S. (2012). The lifelong effects of early childhood adversity and toxic stress. Pediatrics. 129(1), e232-46.

19. Turecki, G., Ernst, C., Jollant, F., Labonte, B., and Mechawar, N. (2012). The neurodevelopmental origins of suicidal behavior. Trends Neurosci. 35(1), 14-23.

20. Balleine, B. W. and O'doherty, J. P. (2010). Human and rodent homologies in action control: corticostriatal determinants of goal-directed and habitual action. Neuropsychopharmacology. 35(1), 48-69.

21. Van Den Bos, W. and Guroglu, B. (2009). The role of the ventral medial prefrontal cortex in social decision making. J Neurosci. 29(24), 7631-2.

22. Coryell, W. and Schlesser, M. (2001). The dexamethasone suppression test and suicide prediction. Am J Psychiatry. 158(5), 748-53.

23. Ridder, S., et al. (2005). Mice with genetically altered glucocorticoid receptor expression show altered sensitivity for stress-induced depressive reactions. J Neurosci. 25(26), 6243-50.

24. Smalheiser, N. R., Lugli, G., Rizavi, H. S., Torvik, V. I., Turecki, G., and Dwivedi, Y. (2012). MicroRNA expression is down-regulated and reorganized in prefrontal cortex of depressed suicide subjects. PLoS One. 7(3), e33201.

25. Morlando, M., Ballarino, M., Gromak, N., Pagano, F., Bozzoni, I., and Proudfoot, N. J. (2008). Primary microRNA transcripts are processed co-transcriptionally. Nat Struct Mol Biol. 15(9), 902-9.

26. Choi, J. K. (2010). Contrasting chromatin organization of CpG islands and exons in the human genome. Genome Biol. 11(7), R70.

27. Bani-Fatemi, A., Goncalves, V. F., Zai, C., De Souza, R., Le Foll, B., Kennedy, J. L., Wong, A. H., and De Luca, V. (2013). Analysis of CpG SNPs in 34 genes: association test with suicide attempt in schizophrenia. Schizophr Res. 147(2-3), 262-8.

28. Keller, S., et al. (2011). TrkB gene expression and DNA methylation state in Wernicke area does not associate with suicidal behavior. J Affect Disord. 135(1-3), 400-4.

29. Labonte, B., et al. (2013). Genome-wide methylation changes in the brains of suicide completers. Am J Psychiatry. 170(5), 511-20.

30. Labonte, B., Yerko, V., Gross, J., Mechawar, N., Meaney, M. J., Szyf, M., and Turecki, G. (2012). Differential glucocorticoid receptor exon 1(B), 1(C), and 1(H) expression and methylation in suicide completers with a history of childhood abuse. Biol Psychiatry. 72(1), 41-8.

31. Murphy, T. M., et al. (2013). Genetic variation in DNMT3B and increased global DNA methylation is associated with suicide attempts in psychiatric patients. Genes Brain Behav. 12(1), 125-32.

32. Fiori, L. M. and Turecki, G. (2011). Epigenetic regulation of spermidine/spermine N1-acetyltransferase (SAT1) in suicide. J Psychiatr Res. 45(9), 1229-35.

---

We claim:

1. A method for predicting suicide attempt and/or suicide ideation by a subject comprising the steps of:
   (a) measuring the DNA methylation level of a CpG located on the minus strand of chromosome 17, at position 57187729, from DNA isolated from a sample collected from the subject, wherein the DNA methylation level is measured using a primer comprising SEQ ID NO:1, SEQ ID NO:2, SEQ ID NO:3, SEQ ID NO:4 or SEQ ID NO:5;
   (b) detecting the genotype at the single nucleotide polymorphism (SNP), rs7208505, from DNA isolated from a sample collected from the subject; and
   (c) using a linear model that utilizes the DNA methylation level, genotype at rs7208505, age and sex to predict suicide attempt and/or suicide ideation by the subject.

2. The method of claim 1, wherein the linear model further utilizes a stress/anxiety metric.

3. The method of claim 2, wherein the stress/anxiety metric comprises the results from a stress/anxiety questionnaire.

4. The method of claim 2, wherein the stress/anxiety metric comprises salivary cortisol measurement from the subject.

5. The method of claim 2, wherein the stress/anxiety metric comprises a biomarker of salivary cortisol measured from the subject.

6. The method of claim 5, wherein the biomarker of salivary cortisol comprises CpG dinucleotide methylation at one or more of the following genes:

EXOC4, KRT6A, MUC1, CLEC18B, MST1P2, ROMO1, MAPK1IP1L, HCRTR1, EPS15, DCHS2, FABP7, HOXC11, SLC26A1, DEXI, AMTN, PNPT1, SLC9A3, NOD2, CDH4, PLA2G7, BCAS3, RBBP5, FAM167A, YKT6, ANKH, CDH22, DGKI, CACNA1H, LRTOMT, SCARF2, KLHL29, MAP4K5, ATL1, MAP4K5, SLC29A4, C14orf180, NOB1, MRAP2, ZNF496, ANGPT1, ABCC8, PTPRN2, GPC5, RNF115, ZDHHC11, PCDHA6, PCDHA2, PCDHA1, PCDHA7, PCDHA1, PCDHA6, PCDHA5, PCDHA9, PCDHA9, PCDHA3, PCDHA4, PCDHA8, GABBR1, SDK1, CAMTA1, SKI, RPS6KC1, GALNT9, SPAG6, HIST2H2BF, SPINT3, KIAA0664, TSNARE1, EPS8L2, PICALM, BCL2L10, HTR3C, CNGA3, DERL1, COL23A1, BACE1, SRPK2, RNF111, SPATA7, FAM189A1, TRIM55, ARMC9, MTHFD1L, and SLC8A2.

7. The method of claim 1, wherein the sample is a blood, serum, or saliva sample.

8. A method for predicting suicide ideation and/or suicide attempt comprising the steps of:
   (a) measuring DNA methylation level at a CpG dinucleotide located in the 3' untranslated region (UTR) of SKA2 from DNA isolated from a sample collected from the subject, wherein the DNA methylation level is measured a primer comprising SEQ ID NO:1, SEQ ID NO:2, SEQ ID NO:3, SEQ ID NO:4 or SEQ ID NO:5;
   (b) detecting the genotype at the SNP rs7208505, from DNA isolated from a sample collected from the subject; and
   (c) using a linear model that incorporates the measured DNA methylation level and genotype to predict suicide attempt and/or suicide ideation.

9. The method of claim 8, wherein the linear model further utilizes age and sex as additive covariates.

10. The method of claim 8, wherein the linear model further utilizes a stress/anxiety metric.

11. The method of claim 10, wherein the stress/anxiety metric comprises the results from a stress/anxiety questionnaire.

12. The method of claim 10, wherein the stress/anxiety metric comprises salivary cortisol measured from the subject or a biomarker thereof.

13. The method of claim 8, wherein the sample is a blood, serum, or saliva sample.

* * * * *

SEQUENCE LISTING

```
<160> NUMBER OF SEQ ID NOS: 11

<210> SEQ ID NO 1
<211> LENGTH: 30
<212> TYPE: DNA
<213> ORGANISM: Artificial Sequence
<220> FEATURE:
<223> OTHER INFORMATION: SKA2_Fo

<400> SEQUENCE: 1
gagaaataag ttatatttta gtattagata                                30

<210> SEQ ID NO 2
<211> LENGTH: 28
<212> TYPE: DNA
<213> ORGANISM: Artificial Sequence
<220> FEATURE:
<223> OTHER INFORMATION: SKA2_Ro

<400> SEQUENCE: 2
aaaataatac aatctaattt ttctccct                                  28

<210> SEQ ID NO 3
<211> LENGTH: 22
<212> TYPE: DNA
<213> ORGANISM: Artificial Sequence
<220> FEATURE:
<223> OTHER INFORMATION: SKA2_Fib

<400> SEQUENCE: 3
gagatggttt tgggatgtga tg                                        22

<210> SEQ ID NO 4
<211> LENGTH: 31
<212> TYPE: DNA
<213> ORGANISM: Artificial Sequence
<220> FEATURE:
<223> OTHER INFORMATION: SKA2_Ri
```

```
<400> SEQUENCE: 4
taactaaaaa caaaaccact tttaatacta a                              31

<210> SEQ ID NO 5
<211> LENGTH: 25
<212> TYPE: DNA
<213> ORGANISM: Artificial Sequence
<220> FEATURE:
<223> OTHER INFORMATION: SKA2_Pyro

<400> SEQUENCE: 5
attataatct ctccataata ctacc                                     25

<210> SEQ ID NO 6
<211> LENGTH: 30
<212> TYPE: DNA
<213> ORGANISM: Artificial Sequence
<220> FEATURE:
<223> OTHER INFORMATION: SKA2_upstream_Fo

<400> SEQUENCE: 6
aattgttttg tttagtttga atattttaag                                30

<210> SEQ ID NO 7
<211> LENGTH: 30
<212> TYPE: DNA
<213> ORGANISM: Artificial Sequence
<220> FEATURE:
<223> OTHER INFORMATION: SKA2_upstream_Ro

<400> SEQUENCE: 7
tatctaatac taaaatataa cttatttctc                                30

<210> SEQ ID NO 8
<211> LENGTH: 24
<212> TYPE: DNA
<213> ORGANISM: Artificial Sequence
<220> FEATURE:
<223> OTHER INFORMATION: SKA2_upstream_Fib

<400> SEQUENCE: 8
tgtttaggtt ggaatgtagt ggta                                      24

<210> SEQ ID NO 9
<211> LENGTH: 26
<212> TYPE: DNA
<213> ORGANISM: Artificial Sequence
<220> FEATURE:
<223> OTHER INFORMATION: SKA2_upstream_Ri

<400> SEQUENCE: 9
cctaatcaaa ataataaaac cccatc                                    26

<210> SEQ ID NO 10
<211> LENGTH: 27
<212> TYPE: DNA
<213> ORGANISM: Artificial Sequence
<220> FEATURE:
<223> OTHER INFORMATION: SKA2_upstream_Pyro

<400> SEQUENCE: 10
ctctactaaa aatacaaaaa aataacc                                   27

<210> SEQ ID NO 11
<211> LENGTH: 17
```

```
<212> TYPE: DNA
<213> ORGANISM: Homo sapiens

<400> SEQUENCE: 11
aactagcatt gactatt                                                   17
```